(12) United States Patent
Berkowitz et al.

(10) Patent No.: US 12,103,950 B2
(45) Date of Patent: Oct. 1, 2024

(54) TRANSGENIC PLANTS THAT OVEREXPRESS A R2R3-MYB TRANSCRIPTION FACTOR GENE AND METHODS FOR PRODUCING THE SAME

(71) Applicant: UNIVERSITY OF CONNECTICUT, Farmington, CT (US)

(72) Inventors: Gerald Berkowitz, Farmington, CT (US); Samuel Haiden, Farmington, CT (US); Yi Ma, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 15 days.

(21) Appl. No.: 18/159,906

(22) Filed: Jan. 26, 2023

(65) Prior Publication Data

US 2023/0287063 A1    Sep. 14, 2023

Related U.S. Application Data

(60) Provisional application No. 63/303,783, filed on Jan. 27, 2022.

(51) Int. Cl.
*C07K 14/415* (2006.01)
*C12N 15/82* (2006.01)

(52) U.S. Cl.
CPC ........ *C07K 14/415* (2013.01); *C12N 15/8223* (2013.01); *C12N 15/8243* (2013.01)

(58) Field of Classification Search
None
See application file for complete search history.

(56) References Cited

U.S. PATENT DOCUMENTS

| | | |
|---|---|---|
| 4,876,276 A | 10/1989 | Mechoulam et al. |
| 5,227,537 A | 7/1993 | Stoss et al. |
| 5,434,295 A | 7/1995 | Mechoulam et al. |

FOREIGN PATENT DOCUMENTS

| | | |
|---|---|---|
| WO | WO 2018/057385 | 3/2018 |

OTHER PUBLICATIONS

Keskin, Ozlem, et al. "A new, structurally nonredundant, diverse data set of protein-protein interfaces and its implications." Protein Science 13.4 (2004): 1043-1055. (Year: 2004).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*
Thornton, Janet M., et al. "From structure to function: approaches and limitations." nature structural biology 7.11 (2000): 991-994. (Year: 2000).*
GenBank Accession XM_010089828.2 "Predicted: Morus notabilis transcription factor MYB16 (LOC21396745), mRNA" dated Feb. 26, 2018 https://www.ncbi.nlm.nih.gov/nuccore/XM_010089828.2/ (Year: 2018).*
Li H et al., "Evolutionary and functional analysis of mulberry type III polyketide synthases.", BMC Genomics, Aug. 4, 2016; 17:540 (Year: 2016).*
GenBank Accession XP_030485058.1 "transcription factor MYB106 [Cannabis sativa]" dated May 18, 2020 https://www.ncbi.nlm.nih.gov/protein/XP_030485058.1 (Year: 2020).*
Xin, Y., Pan, W., Chen, X et al. Transcriptome profiling reveals key genes in regulation of the tepal trichome development in Lilium pumilum D.C.. Plant Cell Rep 40, 1889-1906 (2021). https://doi.org/10.1007/s00299-021-02753-x (Year: 2021).*
Agurell et al., Pharmacokinetics and metabolism of delta 1-tetrahydrocannabinol and other cannabinoids with emphasis on man. Pharmacol Rev. Mar. 1986;38(1):21-43.
Apicella et al., Delineating genetic regulation of cannabinoid biosynthesis during female flower development in Cannabis sativa. Plant Direct. Jun. 8, 2022;6(6):e412. 8 pages.
Batzer et al., Enhanced evolutionary PCR using oligonucleotides with inosine at the 3'-terminus. Nucleic Acids Res. Sep. 25, 1991; 19(18): 5081.
Consroe et al., Antiepileptic potential of cannabidiol analogs. J Clin Pharmacol. Aug.-Sep. 1981;21(S1):428S-436S.
Glover et al., Development of several epidermal cell types can be specified by the same MYB-related plant transcription factor. Development. Sep. 1998;125(17):3497-508.
Guo et al., Evaluation of reference genes for RT-qPCR analysis in wild and cultivated Cannabis. Biosci Biotechnol Biochem. Nov. 2018;82(11):1902-1910.
Lashbrooke et al., The Tomato MIXTA-Like Transcription Factor Coordinates Fruit Epidermis Conical Cell Development and Cuticular Lipid Biosynthesis and Assembly. Plant Physiol. Dec. 2015;169(4):2553-71.
Livingston et al., Cannabis glandular trichomes alter morphology and metabolite content during flower maturation. Plant J. Jan. 2020;101(1):37-56.
Matias-Hernandez et al., Flowering and trichome development share hormonal and transcription factor regulation. J. Exp. Bot, 2016, 67(5), 1209-1219.
Ohtsuka et al., An alternative approach to deoxyoligonucleotides as hybridization probes by insertion of deoxyinosine at ambiguous codon positions. J Biol Chem. Mar. 10, 1985;260(5):2605-8.
Oshima et al., MIXTA-like transcription factors and WAX INDUCER1/SHINE1 coordinately regulate cuticle development in *Arabidopsis* and Torenia fournieri. Plant Cell. May 2013;25(5):1609-24.
Payne et al., Heterologous myb genes distinct from GL1 enhance trichome production when overexpressed in Nicotiana tabacum. Development. Feb. 1999;126(4):671-82.
Pouwels et al., Cloning Vectors, A Laboratory Manual, Elsevier, Amsterdam. 1987 TOC only. 4 pages.

(Continued)

*Primary Examiner* — Charles Logsdon
*Assistant Examiner* — Kelsey L McWilliams
(74) *Attorney, Agent, or Firm* — Casimir Jones SC; Lisa Mueller

(57) ABSTRACT

The present disclosure provides compositions and methods related to genetically engineered plants. In particular, the present disclosure provides novel compositions for transgenic cannabis plants that overexpress a R2R3-MYB transcription factor gene and methods related to the genetic regulation of the development of a glandular trichome in plants.

27 Claims, 7 Drawing Sheets
(7 of 7 Drawing Sheet(s) Filed in Color)

Specification includes a Sequence Listing.

(56) References Cited

OTHER PUBLICATIONS

Rossolini et al., Use of deoxyinosine-containing primers vs degenerate primers for polymerase chain reaction based on ambiguous sequence information. Mol Cell Probes. Apr. 1994;8(2):91-8.

Schardl et al., Design and construction of a versatile system for the expression of foreign genes in plants. Gene, 1987, 61(1), 1-11.

Schena et al., A steroid-inducible gene expression system for plant cells. Proc Natl Acad Sci U S A. Dec. 1, 1991; 88(23): 10421-10425.

Shi et al., The roles of AaMIXTA1 in regulating the initiation of glandular trichomes and cuticle biosynthesis in Artemisia annua. New Phytol. Jan. 2018;217(1):261-276.

Thompson et al., Characterization of the herbicide-resistance gene bar from Streptomyces hygroscopicus. EMBO J. Sep. 1987;6(9):2519-23.

Uzelac et al., Glandular Trichomes on the Leaves of Nicotiana tabacum: Morphology, Developmental Ultrastructure, and Secondary Metabolites. Plant Cell and Tissue Differentiation and Secondary Metabolites, 2020, 1-37.

Voinnet et al., An enhanced transient expression system in plants based on suppression of gene silencing by the p19 protein of tomato bushy stunt virus. Plant J. Mar. 2003;33(5):949-56.

Ward et al., Chemical regulation of transgene expression in plants. Plant Mol Biol. May 1993;22(2):361-6.

Xu et al., The land plant-specific MIXTA-MYB lineage is implicated in the early evolution of the plant cuticle and the colonization of land. New Phytol. Feb. 2021;229(4):2324-2338.

Yan et al., A novel HD-ZIP IV/MIXTA complex promotes glandular trichome initiation and cuticle development in Artemisia annua. New Phytol. Apr. 2018;218(2):567-578.

Zheng et al., The cauliflower mosaic virus (CaMV) 35S promoter sequence alters the level and patterns of activity of adjacent tissue- and organ-specific gene promoters. Plant Cell Rep., 2007, 26, 1195-1203.

* cited by examiner

FIG. 1A
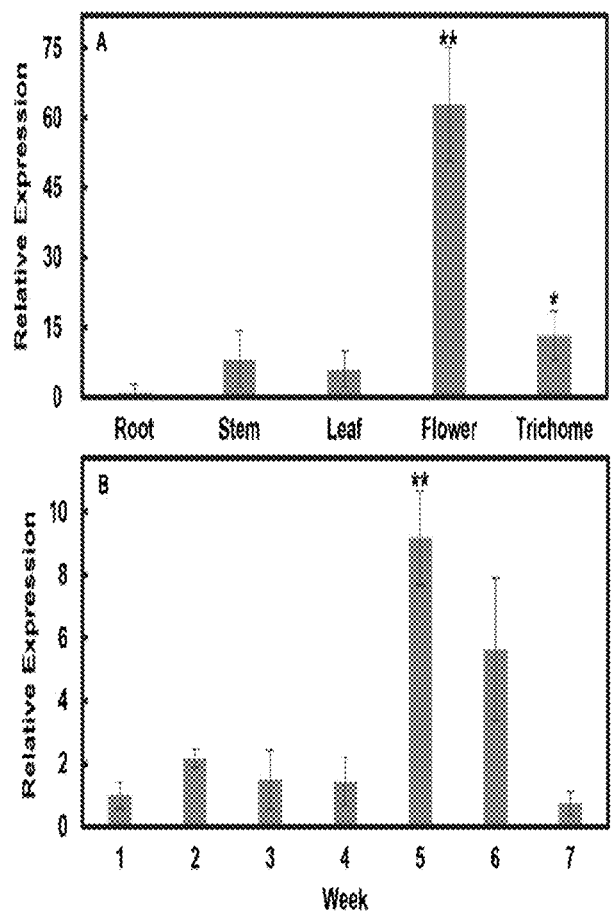
FIG. 1B
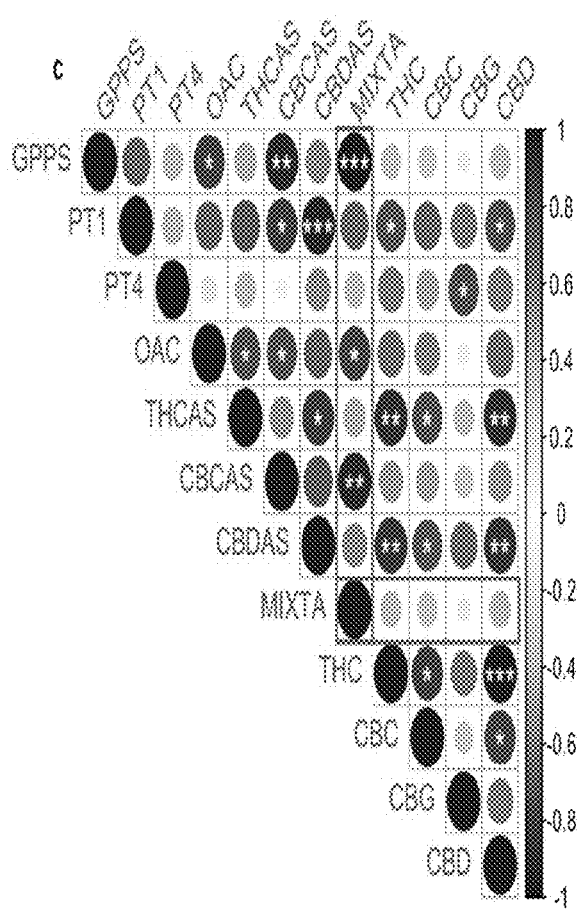
FIG. 1C

FIG. 4A 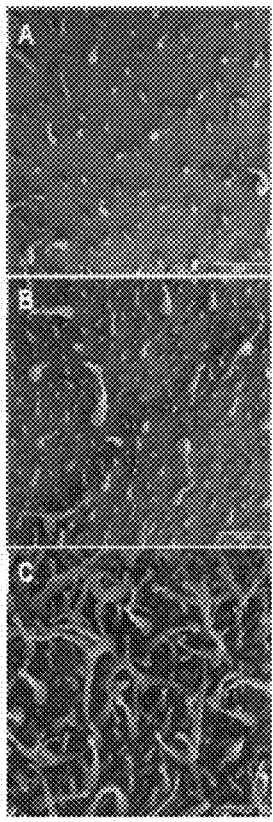 FIG. 4D 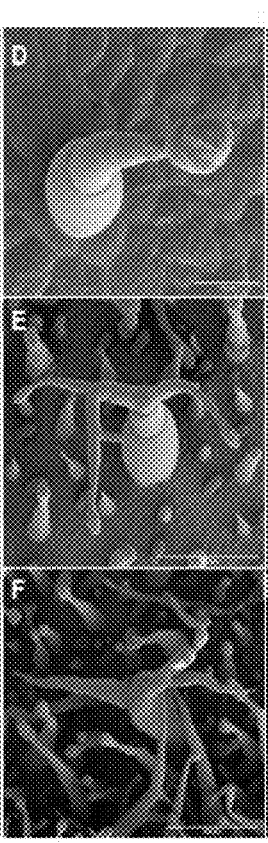 FIG. 4G 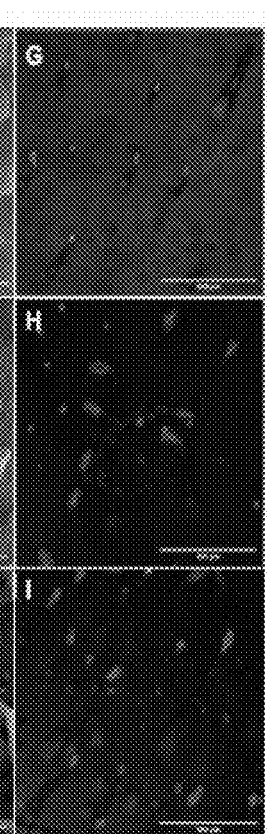
FIG. 4B 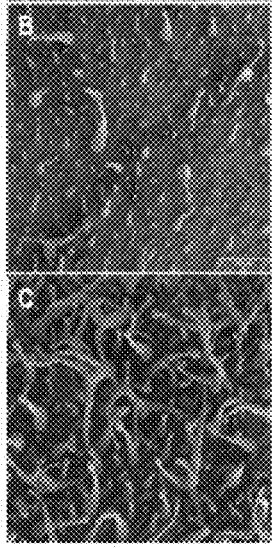 FIG. 4H
FIG. 4C 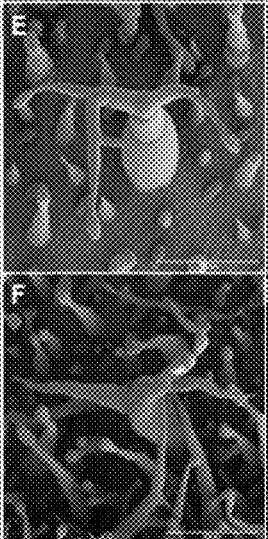 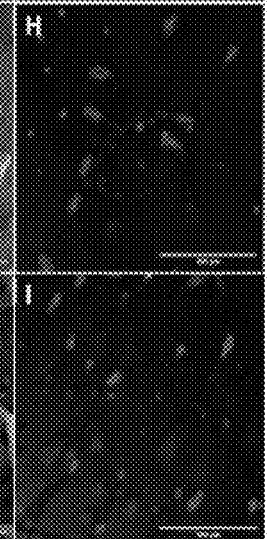 FIG. 4I
FIG. 4E (middle pane)
FIG. 4F (bottom middle pane)

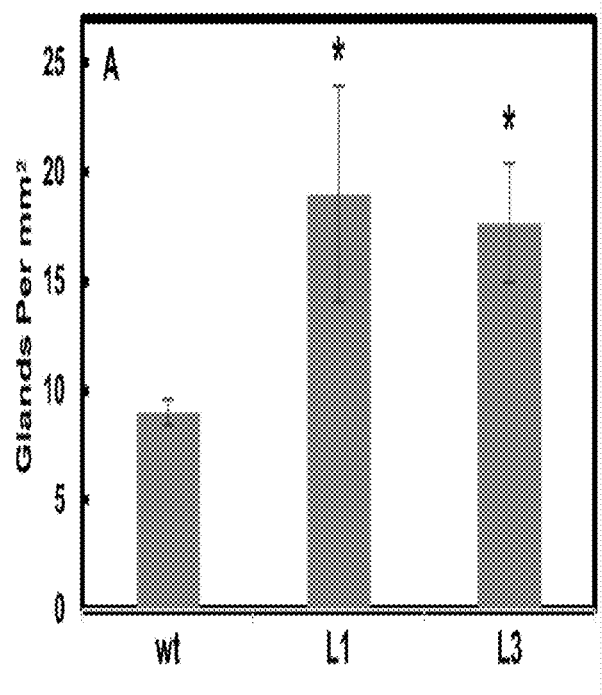
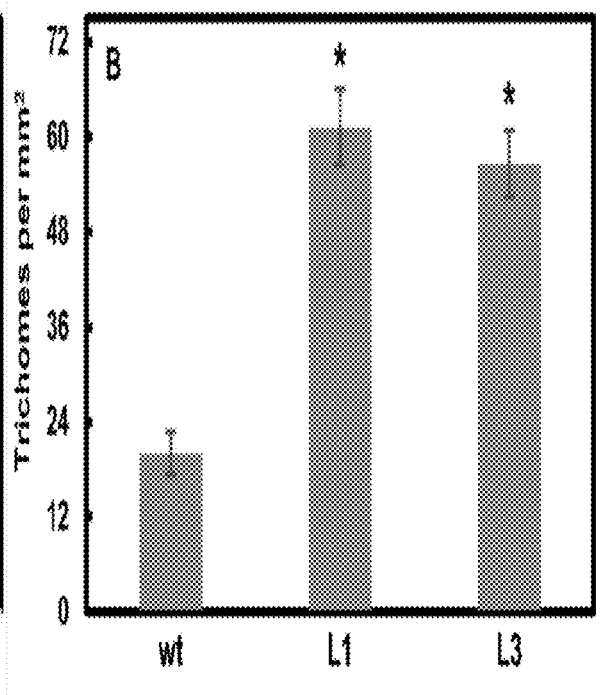
FIG. 5A
FIG. 5B

```
                            SEQUENCE LISTING

Sequence total quantity: 5
SEQ ID NO: 1            moltype = AA  length = 1475
FEATURE                 Location/Qualifiers
REGION                  1..1475
                        note = Synthetic
source                  1..1475
                        mol_type = protein
                        organism = synthetic construct
SEQUENCE: 1
ATTGATGTCT CCTTCTTATC CCATTTAAAT CGCTGACCTT CCTCTTCCTA TTCCCATCTC   60
TATTCATTTT TCATTTTTAT TCATCAAAAA AAAAAAAAAA CTCATATACT CTTTCTCTCT  120
CTGTCTAATT TTCTTATATT GTATCATCAT CATCATCGCT ATTATAATAC ATATAGATCG  180
ATCATATATA TATATATATA TGGGTCGGTC ACCATGCTGC GACAAAGTGG GATTGAAGAA  240
AGGGCCATGG ACACCTGAAG AAGACCAAAA GCTCTTGGCT TATATCGAAC AACATGGCCA  300
TGGAAGTTGG CGAGCTTTAC CCGCTAAAGC AGGGCTTCAA AGATGTGGAA AGAGTTGTAG  360
ACTAAGATGG ACTAATTATT TAAGACCTGA TATAAAGAGA GGCAAGTTCA GTTTGCAAGA  420
AGAACAAACC ATTATTCAAC TCCATGCTTT ACTAGGCAAC AGGTGGTCGG CTATAGCAAC  480
TCATTTGGCA AAAAGAACAG ATAATGAAAT AAGAATTAT TGGAACACAC ATCTAAAGAA   540
ACGTTTAGCC AAAATGGGAA TTGACCCAAT TACCCACAAA CCAAAGAACG ACAATCTTCT  600
CTCTCAACAA GACGGTGGTC AATCCAAGAA CGCCGCTAAC TTAAGCCACA TGGCTCAGTG  660
GGAAAGCGCT CGGCTCGAAG CCGAAGCTCG GCTCGTTAGA GAGTCCAAGC TTCGTACCAC  720
TACCAACAAC AATATCATTC ATCATCATAA TCATTTCTTC CTTCATCATA ATCTCATCAA  780
CAACAACACT ACCATCGGCT CGGCTTCAGC TTCATCAGCT TCGGCTTCAA CTCACCTTAT  840
TGACAAAACG ACGTCGTCTT CCCATAATAA CGTGTTTATT GAGTCTGCCA CGTGGAACAA  900
TACTAGTGGT GGTGGTGGGG TCCGCAGTGA CCTTGAGTCA CCCACATCTA CATTAACATT  960
TTCTGAGAAC GCGCCGCCGT CCGTGGCTGC CGGAGATACT ACTACCGCCA CCGCCTCGGA 1020
GAGTAATGGT GAGATCTTTA AGAAGAATA TTTGGGAGAA CAAAATTGGA AAGGTAATAA  1080
TAATAATAAA AATTGTGAAG AAGAGGAAGA TGAAGATGGA TTAGATGATA ATAATAATTC 1140
ATTAATGTTG TCATTTAATA TTAATGGAGA TCATCAAGGC TTTACTAGTC TTTTGCTTAA 1200
TAATAATATC TCCGAGGAGC CTAGCTGTTC CGGTGGCGGT GGCGCCAAAA ATGGTGGTGG 1260
TGGTGGTGGA AGTGGAAGTA GTGAACATAA TAATTATGGA GATAATGAGA ATTATTGAAA 1320
TAGTATTCTC AATTTGGTGA ATTCTTCTCC TTCAGATTCT CCTATGTTCT AATTCAGTAT 1380
GTATAATGTA GTAGCTATAT TATAAGAACC CTAGTTAAAT TAAAGAACAC TTTTTCTTTG 1440
TTTAATTTTA ATGTTAATTA TTATATTGTG ATTAA                            1475

SEQ ID NO: 2            moltype = AA  length = 22
FEATURE                 Location/Qualifiers
REGION                  1..22
                        note = Synthetic
source                  1..22
                        mol_type = protein
                        organism = synthetic construct
SEQUENCE: 2
TCCATGCTTT ACTAGGCAAC AG                                             22

SEQ ID NO: 3            moltype = AA  length = 20
FEATURE                 Location/Qualifiers
REGION                  1..20
                        note = Synthetic
source                  1..20
                        mol_type = protein
                        organism = synthetic construct
SEQUENCE: 3
CCACCGTCTT GTTGAGAGAG                                                20

SEQ ID NO: 4            moltype = AA  length = 41
FEATURE                 Location/Qualifiers
REGION                  1..41
                        note = Synthetic
source                  1..41
                        mol_type = protein
                        organism = synthetic construct
SEQUENCE: 4
CAGTCGACTG GATCCGGTAC CATGGGTCGG TCACCATGCT G                        41

SEQ ID NO: 5            moltype = AA  length = 41
FEATURE                 Location/Qualifiers
REGION                  1..41
                        note = Synthetic
source                  1..41
                        mol_type = protein
                        organism = synthetic construct
```

```
SEQUENCE: 5
GAAAGCTGGG TCTAGATATC TCGAGAACAT AGGAGAATCT G                                41
```

TRANSGENIC PLANTS THAT OVEREXPRESS A R2R3-MYB TRANSCRIPTION FACTOR GENE AND METHODS FOR PRODUCING THE SAME

RELATED APPLICATION INFORMATION

This application claims priority to U.S. Application No. 63/303,783, filed on Jan. 27, 2022, the contents of which are herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,865 Byte XML file named "40267_202_ST26.XML," created on Jan. 23, 2023.

TECHNICAL FIELD

The present disclosure relates transgenic plants that overexpress a R2R3-MYB transcription factor gene and methods for increasing or upregulating trichome formation in plants.

BACKGROUND

Glandular trichomes are epidermal outgrowths characterized by the presence of a secretory cavity or "gland", which houses secretory gland cells capable of synthesizing secondary metabolites and exporting them into asecretory reservoir. Glandular stalked trichomes (GST) on cannabis female flowers emerge from an epidermal cell and develop multicellular stalks which are usually less than 500 µm long. In cannabis, glandular trichomes contain a rosette of secretory cells that synthesize and export biosynthetic enzymes into the secretory reservoir. The direct precursor of cannabinoids, cannabigerol (CBG), is synthesized in the plastid of the secretory gland cell, and then exported into the secretory reservoir, where it is converted to tetrahydrocannabinolic acid (THCA), cannabidiolic acid (CBDA), or cannabichromenic acid (CBCA) by their respective synthases.

Current models indicate that the regulation of secondary metabolite production is associated with the regulation of flowering and trichome development (Livingston et al., 2020; Matías-Hernández et al., 2016). After an epidermal cell receives a signal to initiate trichome morphogenesis, it develops into a sessile glandular trichome. In concert with the maturation of the flower, sessile trichomes will develop into the bulbous phase and then eventually reach the capitate-stalked-glandular (CSG) phase. This is the mature phase at which cannabinoids are predominantly produced.

A complex of transcription factors (TFs) in the R2R3-MYB and HD-ZIP IV families has been shown to regulate the development of glandular trichomes in other plant species. This complex includes MIXTA-like proteins, which interact with other HD-ZIP IV TF's to coordinate trichome development in concert with flower development. Understanding the genetic regulation of the development of a glandular trichome from sessile to stalked is of particular importance for cannabis biology, because it has been shown that cannabinoids are not produced in any considerable amount until the trichome reaches the CG phase.

In cannabis, the genetic regulation of glandular trichome initiation is still unknown.

SUMMARY

In one embodiment, the present disclosure relates to recombinant nucleic acid molecule comprising:
a) a nucleotide sequence encoding a R2R3-MYB transcription factor from *Cannabis sativa* having a nucleic acid sequence of SEQ ID NO:1 or a nucleotide sequence having at least 85% identity to the nucleic acid sequence of SEQ ID NO:1; and
b) a nucleotide sequence encoding a heterologous promoter,
wherein the nucleotide sequence encoding the R2R3-MYB transcription factor is operably linked to the nucleotide sequence encoding the heterologous promoter.

In one aspect, the R2R3-MYB transcription factors is MIXTA, such as a MIXTA from *Cannabis sativa*.

In one aspect, the nucleotide sequence encoding the R2R3-MYB transcription factor has at least 86%, 87%, 88%, 89%, 90%, 91%, 92%, 93%, 94%, 95%, 96%, 97%, 98%, 99%, or 100% identity to SEQ ID NO:1.

In another aspect, the promoter is a ubiquitin promoter or a trichome specific promoter.

In another embodiment, the present disclosure relates to an expression vector comprising the above recombinant nucleic acid molecule.

In yet another embodiment, the present disclosure relates to a genetically engineered host cell comprising above expression vector. In some aspects, the genetically engineered host cell is a *Cannabis sativa* cell or a *Nicotiana tabacum* cell.

In yet another embodiment, the present disclosure relates to a genetically engineered plant or plant cell comprising a chimeric gene integrated into its genome, the chimeric gene comprising a nucleotide sequence encoding a R2R3-MYB transcription factor and having a nucleic acid sequence of SEQ ID NO:1 or a nucleotide sequence having at least 85% identity to the nucleic acid sequence of SEQ ID NO:1 operably linked to homologous or heterologous promoter. In some aspects, the nucleotide sequence encoding the R2R3-MYB transcription factor in the genetically engineered plant or plant cell has at least 86%, 87%, 88%, 89%, 90%, 91%, 92%, 93%, 94%, 95%, 96%, 97%, 98%, 99%, or 100% identity to SEQ ID NO:1. In still yet another aspect, the promoter in the genetically engineered plant or plant cell is a ubiquitin promoter or a trichome specific promoter. Still yet other aspects, the genetically engineered plant or plant cell is *Cannabis sativa*. In still further aspects, when the genetically engineered plant is *Cannabis sativa*, it produces increased Δ9 tetrahydrocannabinol (THC), cannabichromene (CBC), cannabidiol (CBD), or any combination thereof when compared to a wildtype or control *Cannabis sativa* plant. In still further aspects, the genetically engineered plant or plant cell comprises a part of a genetically engineered plant.

In still another embodiment, the present disclosure relates to a method of increasing or upregulating trichome formation in a plant. The method comprises the steps of:
a) transforming a plant with a nucleotide sequence that encodes a R2R3-MYB transcription factor and has a nucleic acid sequence of SEQ ID NO:1 or a nucleotide sequence having at least 85% identity to the nucleic acid sequence of SEQ ID NO:1; and
b) growing the plant under conditions which allow for expression of SEQ ID NO:1,
wherein expression of the R2R3-MYB transcription factor in the plant increases or upregulates trichome formation in the plant when compared to a wildtype or control plant.

In one aspect in the above method, the plant is transformed with an expression vector comprising:
the nucleotide sequence encoding a R2R3-MYB transcription factor having the nucleic acid sequence of SEQ ID NO:1 or a nucleotide sequence having at least 85% identity to the nucleic acid sequence of SEQ ID NO:1; and
a nucleotide sequence encoding a heterologous promoter, wherein the nucleotide sequence encoding the R2R3-MYB transcription factor is operably linked to the nucleotide sequence encoding a heterologous promoter.

In another aspect, the nucleotide sequence encoding a R2R3-MYB transcription factor has at least 86%, 87%, 88%, 89%, 90%, 91%, 92%, 93%, 94%, 95%, 96%, 97%, 98%, 99%, or 100% identity to SEQ ID NO:1. In still another aspect, the promoter used in the expression vector in the method is a ubiquitin promoter or a trichome specific promoter. In still another aspect, the plant in the above method is *Cannabis sativa* or a *Nicotiana tabacum*. In yet still another aspect, the plant in the above method is transformed using *Agrobacterium* Ti-plasmid mediated transformation.

In still another embodiment, the present disclosure relates to a genetically engineered plant or plant part produced by above-described method. In one aspect, the genetically engineered plant or plant part is from *Cannabis sativa* or a *Nicotiana tabacum*. In still yet another aspect, when the genetically engineered plant or plant part is *Cannabis sativa*, the genetically engineered plant or plant part contains increased Δ9 tetrahydrocannabinol (THC), cannabichromene (CBC), cannabidiol (CBD), or any combination thereof when compared to a wildtype or control *Cannabis sativa* plant.

In still yet another embodiment, the present disclosure relates to a method of increasing cannabinoid formation in a plant. The method comprises the steps of:
a) transforming a cannabinoid producing plant with a nucleotide sequence that encodes a R2R3-MYB transcription factor and has a nucleic acid sequence of SEQ ID NO:1 or a nucleotide sequence having at least 85% identity to the nucleic acid sequence of SEQ ID NO:1; and
b) growing the plant under conditions which allow for expression of the R2R3-MYB transcription factor,
wherein, expression of the R2R3-MYB transcription factor in the plant: (i) increases or upregulates trichome formation in the plant; and (ii) increases or upregulates the formation of a cannabinoid in the plant.

In one aspects of the above method, the plant is transformed with an expression vector comprising:
the nucleotide sequence encoding a R2R3-MYB transcription factor and having the nucleic acid sequence of SEQ ID NO:1 or a nucleotide sequence having at least 85% identity to the nucleic acid sequence of SEQ ID NO:1; and
a nucleotide sequence encoding a heterologous promoter, wherein the nucleotide sequence encoding the R2R3-MYB transcription factor is operably linked to the nucleotide sequence encoding a heterologous promoter.

In yet another aspect, the nucleotide sequence encoding the R2R3-MYB transcription factor has at least 86%, 87%, 88%, 89%, 90%, 91%, 92%, 93%, 94%, 95%, 96%, 97%, 98%, 99%, or 100% identity to SEQ ID NO:1. In still another aspect, the promoter used in the expression vector in the method is a ubiquitin promoter or a trichome specific promoter. In still another aspect, the plant in the above method is *Cannabis sativa* or a *Nicotiana tabacum*. In yet still another aspect, the plant in the above method is transformed using *Agrobacterium* Ti-plasmid mediated transformation.

In still another embodiment, the present disclosure relates to a genetically engineered plant or plant part produced by above-described method. In one aspect, the genetically engineered plant or plant part is from *Cannabis sativa* or a *Nicotiana tabacum*. In still yet another aspect, when the genetically engineered plant or plant part is *Cannabis sativa*, the genetically engineered plant or plant part contains increased Δ9 tetrahydrocannabinol (THC), cannabichromene (CBC), cannabidiol (CBD), or any combination thereof when compared to a wildtype or control *Cannabis sativa* plant.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows the expression analysis of CsMITZA. FIG. 1A shows the relative expression of CsMIXTA in 5 different tissue types harvested from Cherry Wine. Standard errors are shown. Results are shown as means±SE (n=4). FIG. 1B shows the relative expression of CsMIXTA over 7 weeks of flowering in a hemp variety Cherry Wine. Standard error is shown. * indicates P<0.05, indicates a P<0.01, which was determined by Student t-test. FIG. 1C shows Pearson's matrix analysis of correlation between expression of CsMIXTA and cannabinoid biosynthetic genes and cannabinoid contents. Green boxes highlight CsMIXTA. Blue indicates a positive correlation, while red indicates a negative correlation. Size and color of circle represent strength of correlation. The figures were generated using the R corrplot package github.com/taiyun/corrplot). (*, P<0.05; , P<0.01; *, P<0.001). Percentage data was arcsine transformed prior to statistical analysis.

FIG. 2A shows the top: yeast cells grown on SD medium lacking tryptophan (W) and histidine (H). Cells expressing CsMIXTA produce healthy cultures, while pAS2 empty vector transformed culture does not. Bottom: yeast cells grown on SD medium lacking W. All cells grew normally including cells transformed with the empty vector (EV).

FIG. 4A shows scanning Electron Microscopy and Fluorescence Microscopy micrographs including SEM images of adaxial leaf surface of wt.

FIG. 4B shows scanning Electron Microscopy and Fluorescence Microscopy micrographs, including transgenic line L3.

FIG. 4C shows scanning Electron Microscopy and Fluorescence Microscopy micrographs, including transgenic line L1.

FIG. 4D shows scanning Electron Microscopy and Fluorescence Microscopy micrographs, including representative glandular trichomes from wt.

FIG. 4E shows scanning Electron Microscopy and Fluorescence Microscopy micrographs, including transgenic line L3.

FIG. 4F shows scanning Electron Microscopy and Fluorescence Microscopy micrographs, including transgenic line L1.

FIG. 4G shows scanning Electron Microscopy and Fluorescence Microscopy micrographs, including Fluorescence Microscopy images of wt.

FIG. 4H shows scanning Electron Microscopy and Fluorescence Microscopy micrographs, including transgenic line L3 captured with a Nikon A1R confocal microscope.

FIG. 4I shows scanning Electron Microscopy and Fluorescence Microscopy micrographs, including transgenic line L1 captured with a Nikon A1R confocal microscope.

All samples were taken from tissue adjacent to the midrib of the third leaf from the apical meristem, and 2 cm from the petiole. In all cases, the images shown for each genotype are representative of other biological replicates. Fluorescence signals indicating glandular trichomes were counted from each tissue sample (n=3). Scale bars in FIG. 4A-4C: 500 μm; in FIG. 4D-FIG. 4F: 200 μm; in G-H: 500 μm.

FIG. 5A shows qPCR results displaying CsMIXTA expression in transgenic lines L1 and L3 vs three wt individuals. The same primers were used as for gene expression results in cannabis. Background signal seen in WT is likely to be non-specific binding, as there are multiple R2R3 MYB TF's native to *N. tabacum*.

FIG. 5B shows the average trichome number per mm squared, observed by intrinsic fluorescence. Averages taken from 3 biological reps (N=3) for each transgenic individual and wild type (WT). * indicates P<0.05, which was determined using Student t-test.

DETAILED DESCRIPTION

Figures 2A, 2B:
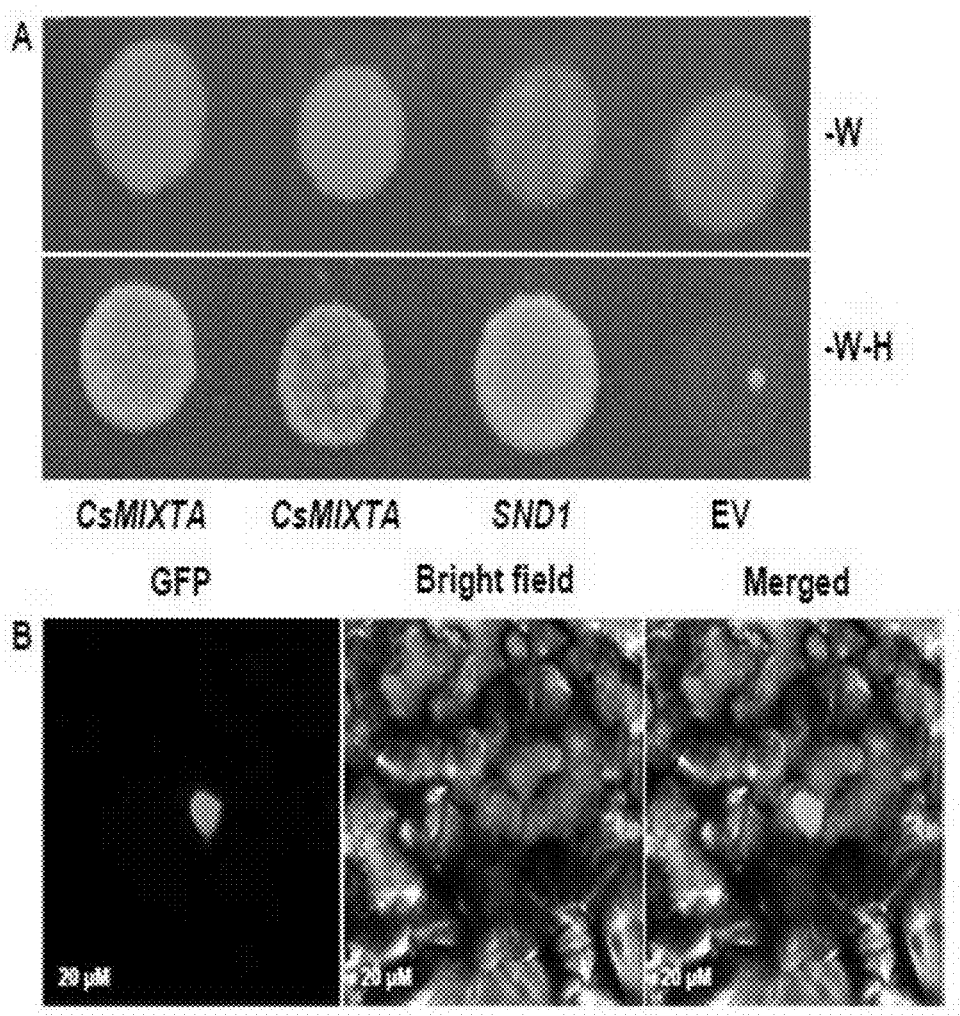
FIG. 2A shows a yeast transactivation assay and subcellular localization of CsMIXTA.
FIG. 2B shows a yeast transactivation assay and subcellular localization of CsMIXTA, including *N. benthamiana* epidermal cells expressing a CsMIXTA-YFP fusion protein, observed using Nikon A1R Confocal microscope with excitation at 488 nm. YFP signal clearly indicates nuclear localization.

The present disclosure relates transgenic (e.g., genetically engineered) plants that overexpress a R2R3-MYB transcription factor gene as well as methods for increasing or upregulating trichome formation in plants.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the singular form "a," "an," and "the" include plural references unless the context clearly dictates otherwise.

As used herein, the terms "about" and "approximately" refer to a quantity, level, value or amount that varies (e.g., plus or minus) by as much as 10% to a reference quantity, level, value or amount.

As used herein, a "cannabinoid" refers to a chemical compound (such as cannabinol, THC or cannabidiol) that is found in the plant species *Cannabis* among others like *Echinacea; Acmella Oleracea; Helichrysum umbraculigerum; Radula marginata* (Liverwort) and *Theobroma cacao*, and metabolites and synthetic analogues thereof that may or may not have psychoactive properties. Cannabinoids can include compounds (such as THC) that have high affinity for the cannabinoid receptor (for example Ki<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol (such as those described in U.S. Pat. No. 5,227,537); (3 S,4R)-7-hydroxy-Δ6-tetrahydrocannabinol homologs and derivatives described in U.S. Pat. No. 4,876,276; (+)-4-[4-DMH-2,6-diacetoxy-phenyl]-2-carboxy-6,6-dimethylbicyclo[3.1.1]hept-2-en, and other 4-phenylpinene derivatives disclosed in U.S. Pat. No. 5,434,295; and cannabidiol (−)(CBD) analogs such as (−)CBD-monomethylether, (−)CBD dimethyl ether; (−)CBD diacetate; (−)3'-acetyl-CBD monoacetate; and ±AF11, all of which are disclosed in Consroe et al., *J. Clin. Phannacol.*, 21:428S-436S, 1981. Other cannabinoids are disclosed in Agurell et al., *Pharmacol. Rev.*, 38:31-43, 1986.

As used herein, the term "cannabinoid" may also include different modified forms of a cannabinoid such as a hydroxylated cannabinoid or cannabinoid carboxylic acid. For example, if a glycosyltransferase were to be capable of glycosylating a cannabinoid, it would include the term cannabinoid as defined elsewhere, as well as the aforementioned modified forms. It may further include multiple glycosylation moieties.

Examples of cannabinoids include tetrahydrocannabinol, cannabidiol, cannabigerol, cannabichromene, cannabicyclol, cannabivarin, cannabielsoin, cannabicitran, cannabigerolic acid, cannabigerolic acid monomethylether, cannabigerol monomethylether, cannabigerovarinic acid, cannabigerovarin, cannabichromenic acid, cannabichromevarinic acid, cannabichromevarin, cannabidolic acid, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid, delta-9-tetrahydrocannabivarin, delta-9-tetrahydrocannabiorcolic acid, delta-9-tetrahydrocannabiorcol, delta-7-cis-iso-tetrahydrocannabivarin, delta-8-tetrahydrocannabiniolic acid, delta-8-tetrahydrocannabinol, cannabicyclolic acid, cannabicylovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxy-cannabitriolvarin, dehydrocannabifuran, cannabifuran, cannabichromanon, cannabicitran, 10-oxo-delta-6a-tetrahydrocannabinol, delta-9-cis-tetrahydrocannabinol, 3, 4, 5, 6-tetrahydro-7-hydroxy-alpha-alpha-2-trimethyl-9-n-propyl-2, 6-methano-2H-1-benzoxocin-5-methanol-cannabiripsol, trihydroxy-delta-9-tetrahydrocannabinol, and cannabinol.

As used herein "expression," as used herein, or "expression of a coding sequence" (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals, such as, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the term "cannabis" or "cannabis plant" refers to any species in the *Cannabis* genus that produces cannabinoids, such as *Cannabis sativa*, hemp, and interspecific hybrids thereof.

As used herein the terms "coding" or "encoding" refers to the process by which a gene, through the mechanisms of transcription and translation, provides information to a cell from which a series of amino acids can be assembled into a specific amino acid sequence to produce a product, such as protein, active enzyme, etc.

As used herein, the terms "gene" or "sequence", as used interchangeably herein, refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (upstream) and following (downstream) the coding region (open reading frame, ORF) as well as, where applicable, intervening sequences (i.e., introns) between individual coding regions (i.e., exons). The term "structural gene" as used herein refers to a DNA sequence that is transcribed into mRNA which is then translated into a sequence of amino acids characteristic of a specific polypeptide.

As used herein, the phrase "heterologous nucleic acid" or "homologous nucleic acid" refer to the relationship between a nucleic acid or amino acid sequence and its host cell or organism, especially in the context of a transgenic organism, such as a transgenic or genetically engineered plant. A homologous sequence is naturally found in the host species (e.g., a cannabis plant transformed with a cannabis gene), while a heterologous sequence is not naturally found in the host cell (e.g., a tobacco plant transformed with a sequence from a cannabis plant). Such heterologous nucleic acids may comprise segments that are a copy of a sequence that is naturally found in the cell into which it has been introduced, or fragments thereof.

As used herein the term "isolated" when used in connection with "isolated nucleic acid" or "isolated nucleic acid molecule" refers to when a nucleic acid, nucleic acid molecule, DNA, or RNA, is removed from its native environment. For example, recombinant DNA or RNA molecules contained in a DNA or RNA construct are considered isolated for the purposes of the present disclosure. Additional examples of isolated DNA or RNA molecules include recombinant DNA molecules maintained in heterologous host cells, DNA or RNA molecules that are purified, partially or substantially, in solution. Isolated nucleic acid molecules also include DNA or RNA molecules produced synthetically.

As used herein, the phrase "host cell" refers to a cell which contains an introduced nucleic acid construct (e.g., a vector, such as an expression vector) and supports the replication and/or expression of the construct.

As used herein the term "marker" refers to a gene that encodes a trait or phenotype that permits the selection of, or the screening for a plant or cell containing the marker. For example, in plants, the marker gene can encode for antibiotic or herbicide resistance. Use of such a marker allows for the selection of transformed cells from cells that are not transformed or transfected.

As used herein, the phrase "MIXTA gene" refers a nucleotide sequence that encodes a R2R3-MYB transcription factor from *Cannabis sativa*, called MIXTA. As used herein, the MIXTA gene is also referred to as the R2R3-MYB transcription factor gene. The gene that encodes for MIXTA or R2R3-MYB transcription factor has the following sequence (the location of the start is shown with underlining and the position of the stop codon is shown in bold): ATTGATGTCTCCTTCTTATCCCATTTAAATCGC-TGACCTTCCTCTTCCTATTCCCATCT CTATTCAT-TTTTCATTTTTATTCATCAAAAAAAAAAAAAAACT-CATATACTCTTTCTC TCTCTGTCTAATTTTCTTATAT-TGTATCATCATCATCATCGCTATTATAATACATATAG ATCGATCATATATATATATATAT<u>ATG</u>GGTCGGTCAC-CATGCTGCGACAAAGTGGGAT TGAAGAAGGGC-CATGGACACCTGAAGAAGACCAAAAGCTCTTGGCT TATATCGAACAACATGGCCATGGAAGTTGGCG-AGCTTTACCCGCTAAAGCAGGGCTT CAAA-GATGTGGAAAGAGTTGTAGACTAAGATGGACTAAT-TATTTAAGACCTGATAT AAAGAGAGGCAAGTTC-AGTTTGCAAGAAGAACAAACCATTATTCAACTC-CATGCTTT ACTAGGCAACAGGTGGTCGGC- TATAGCAACTCATTTGGCAAAAAGAACAGATAATG
AAATAAAGAATTATTGGAACACACATCTAAAG-
AAACGTTTAGCCAAAATGGGAA TTGACCCAAT-
TACCCACAAACCAAAGAACGACAATCTTCTCTCT-
CAACAAGACGGTG GTCAATCCAAGAACGCCG-
CTAACTTAAGCCACATGGCTCAGTGG-
GAAAGCGCTCGG CTCGAAGCCGAAGCTCGGCT-
CGTTAGAGAGTCCAAGCTTCGTACCACTAC-
CAACAA CAATATCATTCATCATCATAATCATTTCT-
TCCTTCATCATAATCTCATCAACAACAAC ACTAC-
CATCGGCTCGGCTTCAGCTTCATCAGCTTCGGCTT-
CAACTCACCTTAT TGACAAAACGACGTCGTCTTCC-
CATAATAACGTGTTTATTGAGTCTGCCACGTGGAA
CAATACTAGTGGTGGTGGTGGGGTCCGCAGTGAC-
CTTGAGTCACCCACATCTACATT AACATTTCT-
GAGAACGCGCCGCCGTCCGTGGCTGCCGGAGA-
TACTACTACCGCCAC CGCCTCGGAGAGTAATGGT-
GAGATCTTTAAAGAAGAATATTTGGGAGAACAA-
AATT GGAAAGGTAATAATAATAATAAAAATTGT-
GAAGAAGAGGAAGATGAAGATGGGTT AGATGA-
TAATAATAATTCATTAATGTTGTCATTTAAATAT-
TAATGGAGATCATCAAGG CTTTACTAGTCTT-
TTGCTTAATAATAATATCTCCGAGGAGCCTAGC-
TGTTCCGGTGGC GGTGGCGCCAAAAATGGTGGT-
GGTGGTGGTGGAAGTGGAAGTAGTGAACATAATAA
TTATGGAGATAATGAGAATTATTGGAATAGTATTCT-
CAATTTGGTGAATTCTTCTCCT TCAGATTCTCC-
TATGTTCTAATTCAGTATGTATAATGTAGTAGCTAT-
ATTATAAGAAC CCTAGTTAAATTAAAGAACAC-
TTTTTCTTTGTTTAATTTTAATGTTAATTATTATATTG
TGATTAA (SEQ ID NO:1) and fragments thereof. Fragments of SEQ ID NO:1 can have a length of 5 contiguous nucleic acids, 10 contiguous nucleic acids, 15 contiguous nucleic acids, 20 contiguous nucleic acids, 25 contiguous nucleic acids, 50 contiguous nucleic acids, 75 contiguous nucleic acids, 100 contiguous nucleic acids, 125 contiguous nucleic acids, 200 contiguous nucleic acids, 250 contiguous nucleic acids, 300 contiguous nucleic acids, 400 contiguous nucleic acids, 500 contiguous nucleic acids, 600 contiguous nucleic acids, 700 contiguous nucleic acids, 800 contiguous nucleic acids, 900 contiguous nucleic acids, 1000 contiguous nucleic acids, 1110 contiguous nucleic acids, 1200 contiguous nucleic acids, 1300 contiguous nucleic acids, 1400 contiguous nucleic acids, or 1450 contiguous nucleic acids.

As used herein, the phrases, "nucleic acid" or "nucleic acid molecules" include single- and double-stranded forms of DNA, single-stranded forms of RNA, and double-stranded forms of RNA (dsRNA). The phrases "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA), whether charged or discharged with a corresponding acylated amino acid), and cRNA (complementary RNA). The term "deoxyribonucleic acid" (DNA) is inclusive of cDNA, genomic DNA, and DNA-RNA hybrids. The phrases "nucleic acid segment" and "nucleotide sequence segment," or more generally, "segment," are understood by those in skilled in the art as functional phrases that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The phrase "nucleic acid molecule" also includes any topological conformation, including single-stranded, double-stranded, partially duplexed, triplexed, hair-pinned, circular, and padlocked conformations.

A "chimeric nucleic acid" comprises a coding sequence linked to a nucleotide sequence that is different from the nucleotide sequence with which it is associated in cells in which the coding sequence occurs naturally.

As used herein, the phrase, "operably linked," when used in reference to a regulatory sequence and a coding (e.g., gene or other nucleotide) sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters, translation leader sequences, introns, enhancers, stem-loop structures, repressor binding sequences, termination sequences, polyadenylation recognition sequences, etc. Regulatory sequences may be located upstream and/or downstream of a coding sequence operably linked thereto. Additionally, particular regulatory sequences operably linked to a coding sequence may be located on the associated complementary strand of a double-stranded nucleic acid molecule.

As used herein, the term "plant" refers to whole plants, plant organs, progeny of whole plants or plant organs, embryos, somatic embryos, embryo-like structures, protocorms, protocorm-like bodies (PLBs), and culture and/or suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). "Plant material", "plant part(s)", or "part from a plant", as used interchangeably herein, refers to any material derived or obtained from a plant such as, for examples, plant organs, embryos, somatic embryos, embryo-like structures, protocorms, protocorm-like bodies (PLBs), and culture and/or suspensions of plant cells.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. Promoters are a type of regulatory sequence or control element. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific."

A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most cell or tissue types.

Any inducible promoter can be used in some embodiments of the present disclosure. See Ward et al. (1993) *Plant Mol. Biol.*, 22:361-366. With an inducible promoter, the rate of transcription increases in response to an inducing agent. Exemplary inducible promoters include, but are not limited to, promoters from the ACEI system that responds to copper, In2 gene from maize that responds to benzenesulfonamide herbicide safeners, tet repressor from Tn10; and the inducible promoter from a steroid hormone gene, the transcriptional activity of which may be induced by a glucocorticosteroid hormone are general examples (Schena et al. (1991) *Proc. Natl. Acad. Sci. USA*, 88:0421).

In some aspects of the disclosure, the promoter can be a ubiquitin promoter. In other aspects, the promoter is a trichome specific promoter. Examples of trichome specific promoters are described in WO 2018/057385.

As used herein, the term "recombinant" when used in reference, for example, to a cell, or nucleic acid, protein, or vector, indicates that the cell, organism, nucleic acid, protein or vector, has been modified by the introduction of a heterologous nucleic acid or protein, or the alteration of a native nucleic acid or protein, or that the cell is derived from a cell so modified. Thus, for example, recombinant cells may express genes that are not found within the native (nonrecombinant or wild-type) form of the cell or express native genes that are otherwise abnormally expressed-over-expressed, under expressed or not expressed at all.

As used herein, the terms "sequence identity" or "identity," when used in the context of two nucleic acid or polypeptide sequences, refers to the residues in the two sequences that are the same when aligned for maximum correspondence over a specified comparison window.

As used herein, the term "trichome" refers to different types of trichomes, both glandular trichomes and/or non-glandular trichomes.

As used herein, the phrase, "trichome cells" refers to the cells making up the trichome structure, such as a gland, or secretory cells, base cells and stalk, or strip cells, extracellular cavity and cuticle cells. Trichomes can also comprise a single (one) cell.

As used herein, the term "transformation" or "genetically modified" refers to the transfer of one or more nucleic acid molecule(s) into a cell. A plant is "transformed" or "genetically modified" by a nucleic acid molecule transduced into the plant when the nucleic acid molecule becomes stably replicated by the plant. Such transformation may be transient or stable. As used herein, the term "transformation" or "genetically modified" encompasses all techniques by which a nucleic acid molecule can be introduced into, such as a plant.

As used herein, the term "vector" refers to a means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria. An "expression vector" is nucleic acid capable of replicating in a selected host cell or organism (e.g., a plant cell or plant). An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette."

A polynucleotide sequence is operably linked to an expression control sequence(s) (e.g., a promoter and, optionally, an enhancer) when the expression control sequence controls and regulates the transcription and/or translation of that polynucleotide sequence.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (See, e.g., Batzer et al., *Nucleic Acid Res.*, 19:5081 (1991); Ohtsuka et al., *J. Biol. Chem.*, 260:2605-2608 (1985); and Rossolini et al., *Mol. Cell. Probes*, 8:91-98 (1994)). Because of the degeneracy of nucleic acid codons, one can use various different polynucleotides to encode identical polypeptides.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Recombinant Nucleic Acid Molecules and Vectors and Genetically Engineered Plants In one embodiment, the present disclosure relates to recombinant nucleic acid molecules. In some aspects, the recombinant nucleic acid molecules are recombinant DNA molecules. In other aspects, the recombinant nucleic acid molecules are RNA molecules. In yet further aspects, the recombinant nucleic acid molecule is an isolated recombinant nucleic acid molecule (such as an isolated recombinant DNA molecule and/or an isolated recombinant RNA molecules).

The recombinant nucleic acid molecules of the present disclosure comprise a nucleotide sequence encoding a R2R3-YB transcription factor from Cannabis sativa known as MIXTA. In some aspects, the nucleotide sequence that encodes the R2R3-YB transcription factor or MIXTA has the nucleic acid sequence shown in SEQ ID NO:1. In other aspects, the nucleotide sequence that encodes the R2R3-YB transcription factor or MIXTA is a fragment of SEQ ID NO:1. In some aspects, a fragment of SEQ ID NO:1 can have a length of 5 contiguous nucleic acids, 10 contiguous nucleic acids, 15 contiguous nucleic acids, 20 contiguous nucleic acids, 25 contiguous nucleic acids, 50 contiguous nucleic acids, 75 contiguous nucleic acids, 100 contiguous nucleic acids, 125 contiguous nucleic acids, 200 contiguous nucleic acids, 250 contiguous nucleic acids, 300 contiguous nucleic acids, 400 contiguous nucleic acids, 500 contiguous nucleic acids, 600 contiguous nucleic acids, 700 contiguous nucleic acids, 800 contiguous nucleic acids, 900 contiguous nucleic acids, 1000 contiguous nucleic acids, 1110 contiguous nucleic acids, 1200 contiguous nucleic acids, 1300 contiguous nucleic acids, 1400 contiguous nucleic acids, or 1450 contiguous nucleic acids. In still further aspects, the nucleotide sequence that encodes the R2R3-YB transcription factor (such as MIXTA) is a nucleotide sequence having at least 85% identity to the nucleic acid sequence of SEQ ID NO:1. In still further aspects, the nucleotide sequence has at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity to SEQ ID NO:1.

In addition to the nucleotide sequence encoding a R2R3-MYB transcription factor (such as a MIXTA gene), or a fragment thereof, the recombinant nucleic acid molecule also comprises a nucleotide sequence encoding at least one promoter. In some aspects, the at least one promoter is a heterologous promoter. In other aspects, the at least one promoter is a homologous promoter. In still further aspects, where the recombinant nucleic acid molecule comprises more than one promoter, each of the promoters may be a heterologous promoters, each may be a homologous promoter, or one may be a heterologous promoter and the other a homologous promoter. In some aspects, the promoter is a constitutive promoter. In other aspects, the promoter is an inducible promoter. In some aspects, the promoter is an ubiquitin promoter. In other aspects, the promoter is a trichome specific promoter. In yet other aspects, the promoter is a leaf promoter or a flower promoter. In still other aspects, the promoter is any suitable promoter facilitating constitutive expression of the open reading frame. The at least one promoter is operably linked to the nucleotide sequence encoding the R2R3-MYB transcription factor gene using routine techniques known in the art.

In addition to the nucleotide sequence encoding a R2R3-MYB transcription factor, or a fragment thereof, the recombinant nucleic acid molecule also comprises a nucleotide sequence encoding at least one reporter protein. In some embodiments, the reporter protein is a green fluorescent protein (GFP).

In another embodiment, the present disclosure relates to recombinant nucleic acid vectors, such as expression vectors, comprising the recombinant nucleic acid molecule described herein. Suitable vectors are well known to those skilled in the art and are described in general technical references such as Pouwels et al., *Cloning Vectors, A Laboratory Manual*, Elsevier, Amsterdam (1986). Vectors for plant transformation have been described in numerous publications, such as, for example, Schardl et al., *Gene*, 61:1-14 (1987). In some aspects, the vector is a plasmid vector or a binary vector. Examples of suitable vectors include Ti plasmid vectors.

Moreover, in addition to containing a nucleotide sequence encoding a R2R3-MYB transcription factor or a fragment thereof, and a promoter, an expression vector can further comprise one or more additional nucleotide sequences (e.g., DNA, cDNA, or RNA) that encode for other heterologous proteins or polypeptides. Such additional nucleotide sequences that encode for other heterologous proteins or proteins can be operably linked to one or more promoters. For example, such one or more additional nucleotide sequences can encode for one or more of olivetol synthase (OLS), olivetolic acid cyclase (OAC), aromatic pyrenyl-transferase (PT), hexanoyl-CoA synthetase (AEE1-1), CBDA synthase, CBCA synthase, THCA synthase or any combination thereof.

Recombinant nucleic acid vectors (e.g., expression vectors) introduce nucleotide sequences of genes (e.g., chimeric genes) under the control of one or more regulatory sequences, such as a promoter. Such vectors can be made using routine techniques known in art. To generate a chimeric gene, an expression vector generally comprises, operably lined in the 5' to 3' direction, a promoter (such as a ubiquitin promoter or a trichome specific promoter), which directs the transcription of the downstream nucleotide sequence that encodes the R2R3-MYB transcription factor (e.g., SEQ ID NO:1, a fragment thereof, or a nucleotide sequence having at least 85% identity to SEQ ID NO:1), and optionally followed by a 3' untranslated nucleic acid region (3'UTR) that encodes a polyadenylation signal which functions in plant cells to cause the termination of transcription and the addition of polyadenylate nucleotides to the 3' end of the mRNA encoding the protein. In addition to the promoter, the recombinant nucleic acid vector can also contain other regulatory elements which include a transcription initiation site, a ribosome binding site, an RNA processing signal, a transcription termination site, and/or a polyadenylation signal (lined in the 5' to 3' direction).

In some other aspects, the recombinant nucleic acid vector (e.g., expression vector) can also contain one or more selectable markers. Selectable markers allow transformed cells to be identified in culture. The marker may be associated with the gene encoding the R2R3-MYB transcription factor. Examples of markers which can be used include: adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3'-0-phosphotransferase (kanamycin, neomycin and G418 resistance). These markers may include resistance to G418, hygromycin, bleomycin, kanamycin, and gentamicin. The vector may also contain the selectable marker gene bar that confers resistance to herbicidal phosphinothricin analogs like ammonium gluphosinate (See, for example, Thompson et al., *EMBO J.,* 9:2519-23 (1987)). Additionally, visible markers such as green florescent protein (GFP) may be used.

In still further aspects, the recombinant nucleic acid vector (e.g., expression vector) can also contain one or more termination sequences, which are positioned downstream of the recombinant nucleic acid molecule described herein. These termination sequences facilitate the termination of transcription and the addition of polyA sequences. Examples of termination sequences that can be used include *Agrobacterium tumefaciens* nopaline synthase terminator (Tnos), *Agrobacterium tumefaciens* mannopine synthase terminator (Tmas), and the CaMV 35S terminator (T35S).

In still yet further aspects, the recombinant nucleic acid vector (e.g., expression vector) also contain enhancers, start codons, splicing signal sequences, replication sequences of bacterial or viral origin (e.g., prokaryotic origin of replication), and targeting sequences.

The recombinant nucleic acid vector (e.g., expression vector) can be introduced into a host (e.g., plant) cell or a plant (such as a cannabinoid or *Cannabis* producing plant (e.g., *Cannabis sativa*)) using routine techniques known in the art. In some aspects, the transformation or transfection includes a stable transformation, a transient expression, or a combination thereof. For example, host cells or plants can be stably transformed or transfected with the nucleic acid vector using standard transformation techniques, such as, Ti-plasmid *Agrobacterium*-mediated transformation, particle bombardment, liposome-mediated transformation, microinjection, polyethylene glycol-assisted protoplast transformation, electroporation or any combination thereof. Such techniques can integrate the chimeric gene contained in the recombinant nucleic acid vector into the genome of a plant or plant cell.

After transformation of the host (e.g., plant) cell or plant, the cells or plants into which the recombinant nucleic acid molecule has been incorporated may be selected by such methods as antibiotic resistance, herbicide resistance, tolerance to amino-acid analogues or using phenotypic markers.

In some aspects, the recombinant nucleic acid vector (e.g., expression vector) described herein is used to transform or transfect a cannabinoid cell or plant, such as a *Cannabis* cell or plant (e.g., *Cannabis sativa*) to produce a genetically engineered (e.g., transgenic) cannabinoid cell or plant. Such genetically engineered plants, when grown under conditions which allow for expression of the nucleotide sequence that encodes the R2R3-MYB transcription factor (e.g., SEQ ID NO:1, a fragment thereof, or a nucleotide sequence having at least 85% identity to SEQ ID NO:1) exhibit an increase or upregulation in trichome formation, as well as density, size and/or branching of stalked glandular trichomes during the growth of the plant when compared to a wildtype or control plant that has not been transformed or transfected with at least one nucleotide sequence that encodes the R2R3-MYB transcription factor and grown under similar conditions.

In some aspects, the "increase" or "upregulation" (e.g., overexpression) in trichome formation is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% more than in a wildtype or control plant that has not been transformed or transfected with at least one nucleotide sequence that encodes the R2R3-MYB transcription factor and is grown under similar conditions. Techniques such as scanning electron microscopy (SEM) can be used to determining whether genetically engineered (e.g., transgenic) plants exhibit an increase or upregulation in trichome formation when compared to the wildtype or control plant grown under similar conditions.

While not wishing to be bound by any theory, it is believed that plants genetically transformed with the recombinant nucleic acid molecule described herein exhibit a higher expression (e.g., overexpression) of the R2R3-MYB transcription factor gene compared to wildtype or control plants that do not contain the recombinant nucleic acid molecule. The overexpression of the R2R3-MYB transcription factor gene (which encodes a transcription factor that initiates trichome development in the female flowers), produces trichomes in the plants that exhibit increased density, size, and/or and branching of stalked glandular trichomes. In cannabinoid producing plants, such as *Cannabis sativa*, the cannabinoids are primarily synthesized and accumulate in the glandular trichomes that are present in high densities on female flowers and at lower densities on male flowers. Thus, an increase in the density, size and/or branching of the stalked glandular trichomes according to the present disclosure results in increased levels of cannabinoids in the disclosed genetically engineered (e.g., transgenic) plants and plant cells.

Thus, the genetically engineered (e.g., transgenic) plants also contain increased amounts of Δ9 tetrahydrocannabinol (THC), cannabichromene (CBC), cannabidiol (CBD), or any combination thereof when compared to a wildtype or control plant that has not been transformed or transfected with at least one nucleotide sequence that encodes a R2R3-MYB transcription factor. In some aspects, the "increase" in the amount of THC, CBC, CBD or any combination thereof is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% more than a wildtype or control plant that has not been transformed or transfected with at least one nucleotide sequence that encodes a R2R3-MYB transcription factor and is grown under similar conditions. Techniques such as gas chromatography, high-performance liquid chromatography, mass spectrometry, flame ionization detection, or any combination thereof can be used to determining whether genetically engineered (e.g., transgenic) plants exhibit increased amounts of Δ9 tetrahydrocannabinol (THC), cannabichromene (CBC), cannabidiol (CBD), or any combination thereof when compared to a wildtype or control plant grown under similar conditions.

Moreover, the above-described genetically engineered (e.g., transgenic) plants can be used in a conventional breeding scheme, such as crossing, selfing, or backcrossing, to produce additional transgenic plants containing the transgene.

3. Methods of the Present Disclosure

In another embodiment, the present disclosure relates to methods of increasing or upregulating trichome formation in a plant. In one aspect, the method involves transforming or transfecting a plant or plant cell with the recombinant nucleic acid molecule described in Section 2. In some aspects, the method involves transforming or transfecting a cannabinoid producing plant or plant cell. In some embodiments, the method involves transforming a plant with a nucleotide sequence that encodes MIXTA and has a nucleic acid sequence of SEQ ID NO:1 or a nucleotide sequence having at least 85% identity to the nucleic acid sequence of SEQ ID NO:1; and a nucleotide sequence encoding a reporter protein such as green fluorescent protein (GFP). In other aspects, the method involves transforming or transfecting a *Cannabis* plant (such as *Cannabis sativa* and/or hemp) or plant cell. In still further aspects, the method involves transforming or transfecting *Nicotiana tabacum* plant or plant cell.

The plant or plant cell is stably transformed or transfected with the recombinant nucleic acid molecule or recombinant nucleic acid vector (e.g., expression vector) as described in Section 2. Once the plant or plant cell is stably transformed with recombinant nucleic acid molecule or recombinant nucleic acid vector, it is grown under conditions which allow for the expression of a R2R3-MYB transcription factor. The growth conditions that allow for the expression of a R2R3-MYB transcription factor are routine and conventional and known to those skilled in the art.

It has been found that plants produced according to the method described herein exhibit an increase or upregulation in trichome formation during the growth of the plant when compared to a wildtype or control plant that has not been transformed or transfected with at least one nucleotide sequence that encodes a R2R3-MYB transcription factor. In some aspects, the "increase" or "upregulation" (e.g., overexpression) in trichome formation is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% more than in a wildtype or control plant that has not been transformed or transfected with at least one nucleotide sequence that encodes a R2R3-MYB transcription factor and is grown under similar conditions. Techniques such as scanning electron microscopy (SEM) can be used to determining whether genetically engineered (e.g., transgenic) plants exhibit an increase or upregulation in trichome formation when compared to the wildtype or control plant grown under similar conditions.

In another embodiment, the present disclosure relates to methods of increasing the density of trichomes, the size of one or more trichomes, and/or the number of branched stalked glandular trichomes in a plant. In one aspect, the method involves transforming or transfecting a plant or plant cell with the recombinant nucleic acid molecule or recombinant nucleic acid vector as described in Section 2. In some aspects, the method involves transforming or transfecting a cannabinoid producing plant or plant cell. In other aspects, the method involves transforming or transfecting a *Cannabis* plant (such as *Cannabis sativa* and/or hemp) or plant cell. In still further aspects, the method involves transforming or transfecting *Nicotiana tabacum* plant or plant cell.

The plant or plant cell is stably transformed or transfected with the recombinant nucleic acid molecule or recombinant nucleic acid vector (e.g., expression vector) described in Section 2. Once the plant or plant cell is stably transformed with recombinant nucleic acid molecule or recombinant nucleic acid vector, it is grown under conditions which allow for the expression of a R2R3-MYB transcription factor. The growth conditions that allow for the expression of a R2R3-MYB transcription factor are routine and conventional and known to those skilled in the art.

It has been found that plants produced according to the methods described herein exhibit an increase in the density of trichomes, the size of one or more trichomes, and/or the number of branched stalked glandular trichomes during the growth of the plant when compared to a wildtype or control plant that has not been transformed or transfected with at least one nucleotide sequence that encodes a R2R3-MYB transcription factor. In some aspects, the "increase" in density of trichomes, size of one or more trichomes, and/or the number of branched stalked glandular trichomes is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% more than in a wildtype or control plant that has not been transformed or transfected with at least one nucleotide sequence that encodes a R2R3-MYB transcription factor and is grown under similar conditions. Techniques such as scanning electron microscopy (SEM) can be used to determine whether genetically engineered (e.g., transgenic) plants exhibit an increase in the density of trichomes, the size of one or more trichomes, and/or the number of branched stalked glandular trichomes compared to the wildtype or control plant grown under similar conditions.

In still yet another embodiment, the present disclosure relates to methods of increasing cannabinoid formation in a plant (e.g., *Cannabis* plant). In one aspect, the method involves transforming or transfecting a cannabinoid producing plant or plant cell with the recombinant nucleic acid molecule or recombinant nucleic acid vector as described in Section 2. In some aspects, the method involves transforming or transfecting a *Cannabis* plant or plant cell. In yet other aspects, the method involves transforming or transfecting a *Cannabis sativa* plant or plant cell. In still other aspects, the method involves transforming or transfecting a hemp plant or plant cell.

The cannabinoid producing plant or plant cell is stably transformed or transfected with the recombinant nucleic acid molecule or recombinant nucleic acid vector (e.g., expression vector) as described in Section 2. Once the cannabinoid producing plant or plant cell is stably transformed with recombinant nucleic acid molecule or recombinant nucleic acid vector, it is grown under conditions which allow for the expression of a R2R3-MYB transcription factor. The growth conditions that allow for the expression of a R2R3-MYB transcription factor are routine and conventional and known to those skilled in the art.

It has been found that cannabinoid plants produced according to the method described herein exhibit increased amounts of Δ9 tetrahydrocannabinol (THC), cannabichromene (CBC), cannabidiol (CBD), or any combination thereof when compared to a wildtype or control plant that has not been transformed or transfected with at least one nucleotide sequence that encodes a R2R3-MYB transcription factor. In some aspects, the "increase" in the amount of THC, CBC, CBD or any combination thereof is about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% more than a wildtype or control plant that has not been transformed or transfected with at least one nucleotide sequence that encodes a R2R3-MYB transcription factor and is grown under similar conditions. Techniques such as gas chromatography, high-performance liquid chromatography, mass spectrometry, flame ionization detection, or any combination thereof can be used to determining whether genetically engineered (e.g., transgenic) plants exhibit increased amounts of Δ9 tetrahydrocannabinol (THC), cannabichromene (CBC), cannabidiol (CBD), or any combination thereof when compared to a wildtype or control plant grown under similar conditions.

It will be readily apparent to those skilled in the art that other suitable modifications and adaptations of the methods of the present disclosure described herein are readily applicable and appreciable, and may be made using suitable equivalents without departing from the scope of the present disclosure or the embodiments disclosed herein. Having now described the present disclosure in detail, the same will be more clearly understood by reference to the following examples, which are merely intended only to illustrate some embodiments of the disclosure, and should not be viewed as limiting to the scope of the disclosure. The disclosures of all journal references, U.S. patents, and publications referred to herein are hereby incorporated by reference in their entireties.

The present disclosure has multiple embodiments, illustrated by the following non-limiting examples.

4. Examples

Materials and Methods

*Cannabis* Plant Growth

Plants acquired from cuttings from mothers in research greenhouses. Cuttings were treated with Hormodin powder and stuck in rockwool cubes soaked with 20 ml/l Clonex Nutrient Solution. Cuttings were allowed to root for 3 weeks before transplant. All plants were grown #600 standard nursery pots filled with Promix-BX25 soilless medium and Osmocote 15-9-12. Plants were grown under 16 hr light/8 hr dark conditions with supplemental lighting from high pressure sodium lighting. Photoperiod was changed to 12 hr light/12 hr dark using blackout curtains. Jack's nutrient solution fed via drip fertigation.

Isolation of RNA and cDNA Synthesis 100 mg plant tissues were collected and immediately frozen in liquid nitrogen. The NucleoSpin Plant and Fungi RNA Isolation Kit (Macherey-Nagel) was used for RNA isolation according to manufacturer's manual. cDNA was synthesized from 1 μg RNA using the iScript Reverse Transcriptase Master Mix (BioRad).

Isolation of *Cannabis* Trichomes

Trichome isolation was performed following the protocol developed by Livingston et al (2020) with slight modifications. Isolation buffer was made as described by Livingston et al but excluding Amberlite. Approximately 3 g of fresh inflorescence tissue was used for trichome isolation. After isolation, the tube containing approximately 100-300 mg of trichome tissue enriched with glands is then frozen at −80° C. until RNA isolation.

Analysis of CsMIXTA Using qPCR qPCR analysis was performed using Bio-Rad CFX. iTaq Universal Sybr Green Master Mix was used (Bio-Rad). For all qPCR reactions, CsUbiquitin was used as the internal reference (Guo et al., 2018). CsMIXTA Primers: forward 5'-TCCATGCTTTACTAGGCAACAG-3' (SEQ ID NO:2), reverse 5'-CCACCGTCTTGTTGAGAGAG-3' (SEQ ID NO:3). Experiments were performed with four biological replicates.

Molecular Cloning of CsMIXTA

CsMIXTA was cloned out of cDNA using iProof HF Master Mix (Bio-Rad). The primers for cloning are forward 5'-CAGTCGACTGGATCCGGTACCATGGGTCGGT-CACCATGCTG-3' (SEQ ID NO:4), reverse 5'-GAAAGCTGGGTCTAGATATCTCGAGAACATAG-GAGAATCTG-3' (SEQ ID NO:5). NEBuilder HiFi DNA Assembly kit (New England Biolabs) was used for the cloning of CsMIXTA into KpnI and XhoI digested pENTR-3C vector (Invitrogen). LR reaction was then performed to clone CsMIXTA into the pB7YWG2 binary vector using LR Clonase II (Invitrogen), as well as the pAS2 and pUBc vectors.

*Agrobacterium* Mediated Transformation of *Nicotiana tabacum*

*N. tabacum* (tobacco) seeds were acquired from Dr. Yi Li at the University of Connecticut. Seeds were sterilized using 3% bleach and 70% ethanol and planted in sterile magenta boxes containing 50 ml full strength Murashige and Skoog (MS) salts (Caisson Labs), MES (adjusted to pH 5.7 with Tris), 1% sucrose, and 1% agar. Seedlings were grown under fluorescent lighting in a growth chamber at 28° C. with a 16-hour photoperiod. Leaves from 3-week-old sterile tobacco plants were used for transformation by *Agrobacterium tumefaciens* GV3101 harboring pB7YWG2-Cs-MIXTA. Tobacco leaf disc transformation was performed as described previously (Zheng et al., 2007). Rooted transformants were transferred to Promix-BX amended with 12 g/gal Osmocote 15-9-12 and maintained in the greenhouse with 16 hr photoperiod.

Yeast Transcriptional Activation Assay

CsMIXTA was fused with the GAL4-BD domain in the pAS2 vector using the LR Clonase II (Invitrogen). The resulting plasmid was transformed into yeast strain AH109 (Clontech) using the Frozen-EZ Yeast Transformation II Kit (Zymo Research). Staphylococcal nuclease domain-containing protein 1 (SND1) (provided by Dr. Huanzhong Wang) was used as a positive control and empty vector as a negative control. The transformed cells were plated on synthetic defined (SD) media to select positive transformants. 4 μl yeast culture harboring corresponding constructs was dropped onto solid SD medium with or without histidine to check for activation of reporter genes. Yeast growth was observed and documented after cultivation at 28° C. for 2 d.

Transient Expression of CsMIXTA-YFP in *N. benthamiana* Leaves

CsMIXTA was fused to YFP using a ubiquitin promoter-containing plasmid (pUBC-YFP) and LR Clonase II (Invitrogen), and the resulting construct was transformed into *Agrobacterium tumefacience* GV3101. Transient transfection protocol was performed as described by Espinoza-atharkar et. al., modified from (Voinnet et al., 2003).

Scanning Electron Microscopy 3 mm squares of tobacco leaf tissue were excised with midribs and veins removed. These squares were fixed for 24 hours in formaldehyde-acetic acid-ethanol (10% formaldehyde, 5% acetic acid, 50% ethanol, 35% MilliQ $H_2O$). These samples were then transferred to a 70% ethanol solution twice, and then dehydrated through a graded ethanol series. Samples were collected and placed into stainless steel containers for critical point drying while completely submerged in 100% ethanol. Dehydrated and dried samples were mounted onto SEM stubs using double-sided carbon tape, and sputter coated with gold nanoparticles. The samples were mounted into a Nova Nanosem 450 and imaged.

Fluorescence and Confocal Microscopy

Samples were mounted between two cover slips and viewed using a Nikon A1R confocal microscope through a 10× Plan Apo lens. Both channels were excited at 488 nm. Emissions collected with GFP filter (488 nm) as well as red filter (700 nm). Z-stacks were collected at a step size of 27 microns. Composite channel/stack images/scale bars were produced in ImageJ. Trichomes were counted in photographs using 'cell counter' in ImageJ.

Results

CsMIXTA is Upregulated During Female Flower Development

Figure 6A:
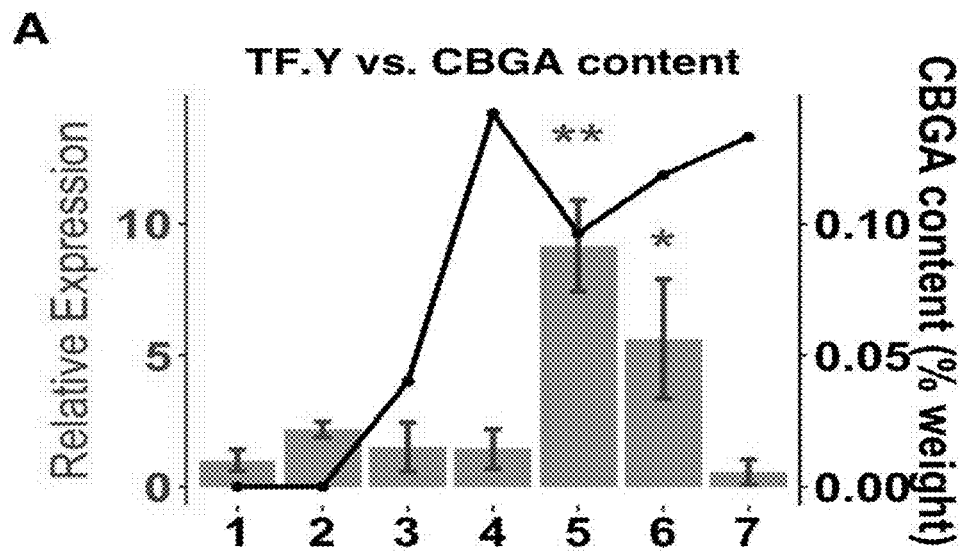
FIG. 6 shows the expression of MIXTA (referred to here as 'TF.Y') in female flowers (bars) as they develop over the seven-week reproductive cycle shown along with increasing cannabinoid content (CBGA in FIG. 6A, CBDA in FIG. 6B) shown as a line.
Figure 6B:
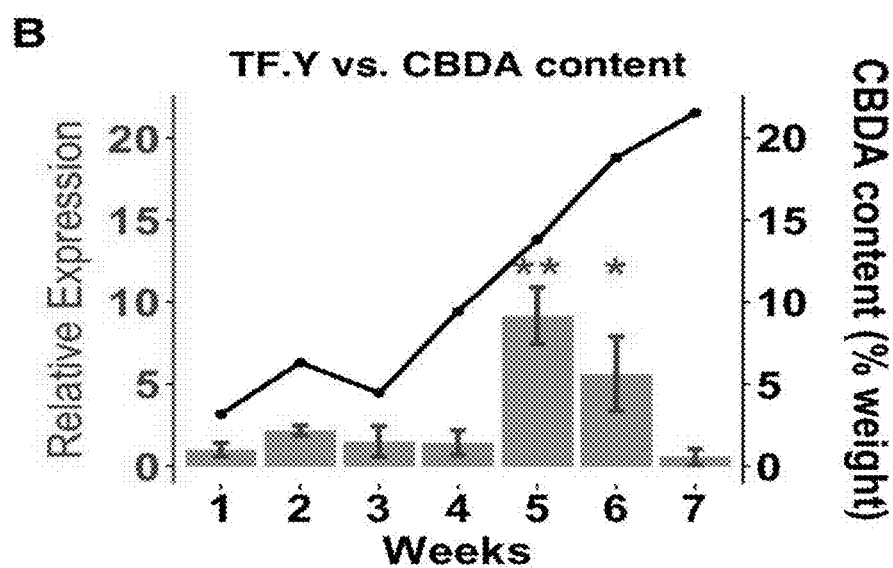

To learn the expression pattern of CsMIXTA in a cannabis plant, CsMIXTA expression was examined in different tissues and during female flower development in a hemp variety Cherry Wine (CW). Different tissue samples were collected in the eighth week of flowering. CsMIXTA is highly expressed in flower tissues compared to the vegetative tissues (FIG. 1A). CsMIXTA is also expressed in stem and leaf tissues, where trichomes are also present. Interestingly, CsMIXTA was also detected in isolated trichomes, suggesting that CsMIXTA may have distinct functions in processes other than trichome development. CsMIXTA expression was further examined during a period of 7-week flower development. The results showed that CsMIXTA was significantly upregulated in week 5 and reduced hereafter (FIG. 1B). CsMIXTA showed a similar expression pattern to that of the enzymes in the cannabinoid biosynthetic pathway (Apicella et al., 2021). Pearson's correlation matrix test was used to evaluate the relationship (positive and negative) between expression of MIXTA and other genes involved in cannabinoid synthesis with expression of cannabinoids across the full seven weeks of flower development (FIG. 1C). This analysis shows that CsMIXTA has a significant positive correlation with the expression of two genes encoding the enzymes (Geranyl Pyrophosphate Synthase (GPPS) and Olivetolic Acid Cyclase (OAC)) required to generate the substrates (GPP and OA) necessary for the synthesis of the first cannabinoid in the biosynthetic pathway (CBG). This analysis indicated that during flower development, CsMIXTA expression was also positively correlated with cannabinoid levels and expression of Cannabichromeic Acid Synthase (CBCAS) which generates the end product cannabinoid CBCa (FIG. 1C). This analysis indicates that through coordinating trichome development, CsMIXTA may play an important role in cannabinoid biosynthesis (See, FIGS. 6A and 6B).

CsMIXTA belongs to the R2R3-MYB TF family and showed homology with the known R2R3-MYB and MIXTA-like TFs from other plant species. Using a yeast activation assay, it was demonstrated that CsMIXTA is capable of transcriptional activation (FIG. 2A). Transient expression of CsMIXTA in N. benthamiana leaves showed nuclear localization (FIG. 2B).

CsMIXTA Promotes Glandular Trichome Formation in Tobacco

Figures 3A, 3B:
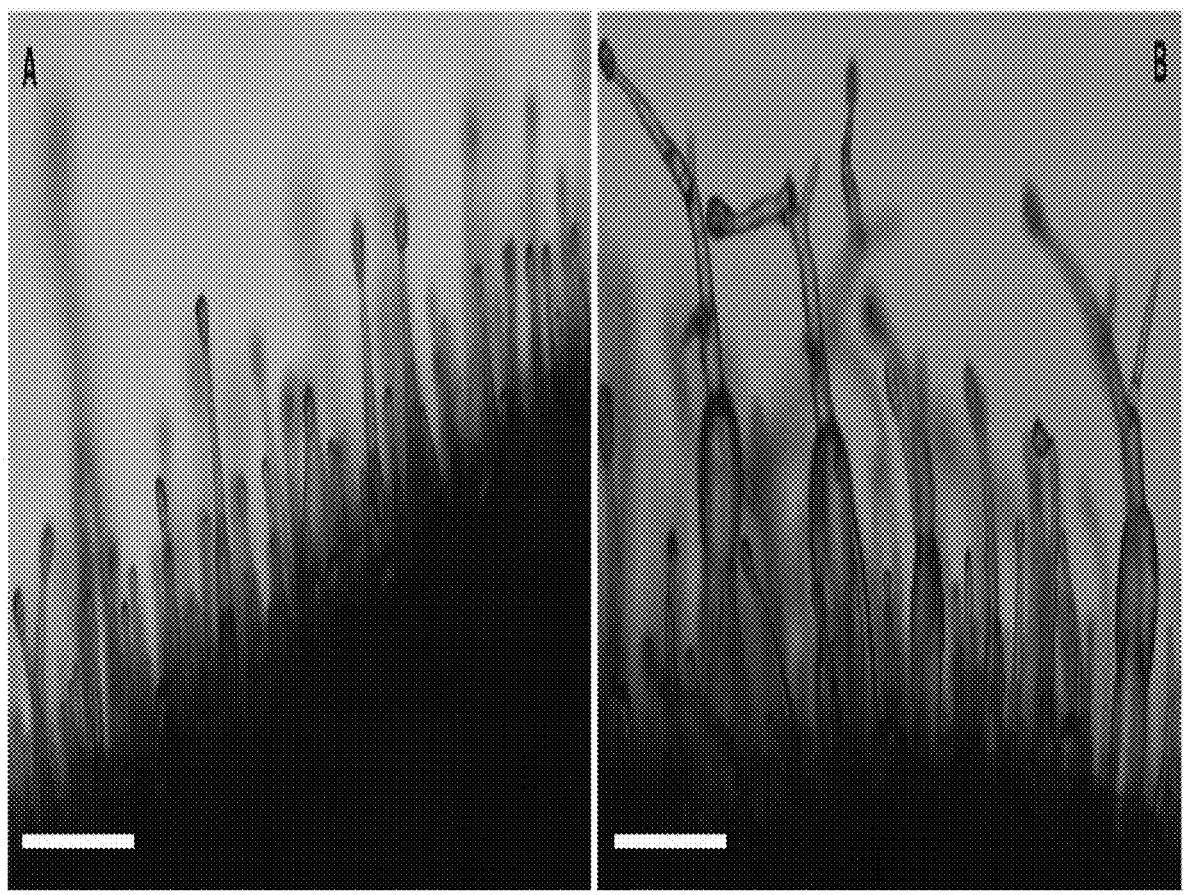
FIG. 3A shows trichomes on wt tobacco leaf edges visualized using a dissection microscope. Samples were viewed at 38× magnification through a dissection microscope.
FIG. 3B shows trichomes on transgenic tobacco leaf edges visualized using a dissection microscope. Samples were viewed at 38× magnification through a dissection microscope. It is noticeable that the base of some trichomes has become enlarged and trichomes are exhibiting nove branching in the transgenic line. Scale bars: 200 μm.
Figure 7A:
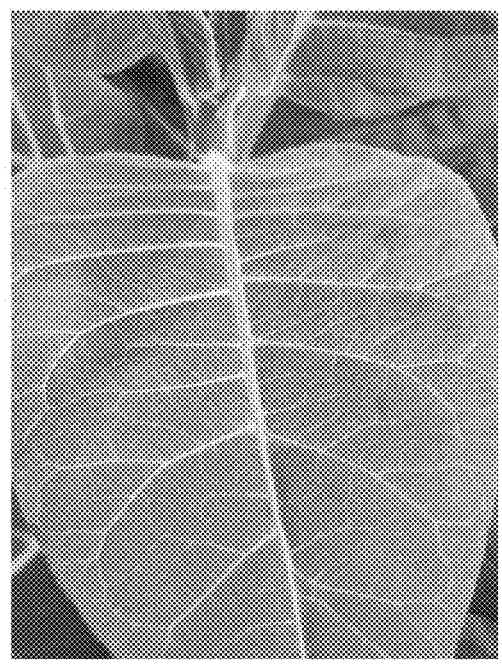
FIG. 7A), or with cannabis MIXTA gene controlled by a constitutive promoter (FIG. 7B). Note that tobacco expressing MIXTA has numerous trichomes in the underside of the leaf (FIG. 7B).
Figure 7B:
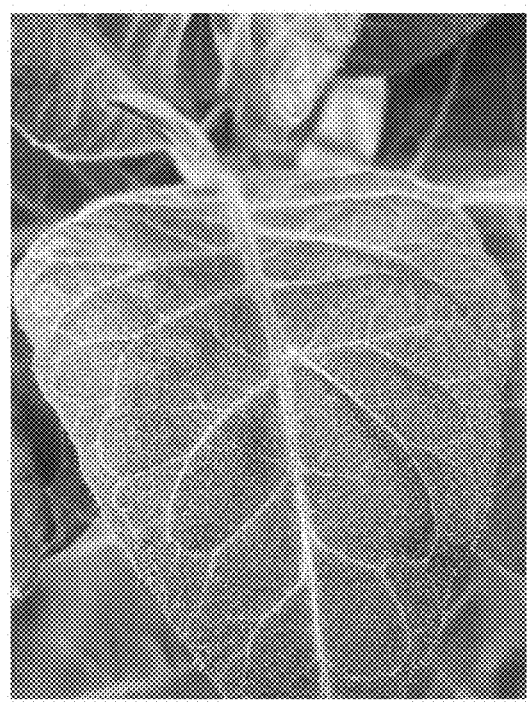
FIG. 7 shows CsMIXTA is a transcription factor gene that regulates production of trichomes. Tobacco leaf transformed with either the empty plasmid (control.

This work of monitoring CsMIXTA expression in cannabis is evidence of an associative relationship between CsMIXTA expression during the maturation of the female flower with cannabinoid synthesis, presumably mediated by CsMIXTA control of trichome development. Further work was undertaken work to examine if this relationship is causal. Cannabis is recalcitrant to genetic transformation; a few reports have been published recently but their transformation effectiveness is not robust. An alternative genetic strategy was used to evaluate the potential causal association of CsMIXTA expression with trichome morphogenesis. Tobacco (Nicotiana tabacum), like cannabis, has glandular stalked trichomes but in the case of tobacco, GSTs are abundant on the leaves (Uzelac et al., 2021). CsMIXTA was ectopically expressed in tobacco plants to understand if it could be involved in glandular trichome morphogenesis. FIG. 3 displays a side view of leaves from wt and a transgenic tobacco line. An increase in trichome size and branching is clearly observed on the transgenic tobacco leaf (FIG. 3; also see FIGS. 7A and 7B).

Trichome morphology on tobacco leaves was further examined using SEM. The two transgenic lines (FIG. 4B, 4C) showed substantially higher trichome density compared to wt (FIG. 4A). Typical wt trichomes possess only one gland and rarely branch (Uzelac et al., 2021). However, highly branched glandular trichomes were observed in both transgenic lines. In addition, trichomes in line 1 (L1) showed higher density, size and branching than line 3 (L3), which could be due to the higher CsMIXTA expression in L1 (FIG. 5A). Floral organs of the transgenic tobacco plants were further investigated. Upper and lower sides of carpel and petal were examined. No differences were observed in trichome number, morphology or distribution on the petals or carpels. Close-up micrographs of representative highly branched glandular trichomes on the transgenic tobacco leaves (FIG. 4E, F) and the regular wt glandular trichome are shown (FIG. 4 D).

Fluorescence microscopy was used to produce intrinsic fluorescence images of the trichomes at the leaf surface (FIG. 4G-4I). Glandular trichome heads filled with secondary metabolites show strong fluorescence: multiple papers have used this method to quantify trichome gland number (Livingston et al., 2020; Shi et al., 2018; Yan et al., 2018). It is clear that the trichome heads were much larger in the two transgenic lines than those in the wt. Trichome counting further showed that trichomes in transgenic tobacco increased nearly 2-fold compared to wt (FIG. 5B). The results indicate that CsMIXTA plays an essential role in glandular trichome initiation and development. These findings provide evidence that CsMIXTA also functions in CSG cells to modulate trichome growth and development, consistent with the higher CsMIXTA expression detected in isolated female flower glandular trichomes (FIG. 1A).

Discussion

In this study, the first TF, CsMIXTA, that influences cannabis CSG development was identified. CsMIXTA is highly expressed in the female cannabis flowers, with expression patterns that are coordinated with cannabinoid biosynthesis and the development of inflorescences. Phylogenetic analysis showed that CsMIXTA is closely related to *Arabidopsis thaliana* AtMYB16 and *Artemisia annua* AaMIXTA. MIXTA-like proteins have been shown to coordinate cuticle deposition in tomato and *Arabidopsis thaliana* (Lashbrooke et al., 2015; Oshima et al., 2013). Modification of AaMIXTA expression altered the biosynthesis of wax and cutin monomers, components of the cuticle (Shi et al., 2018), and MIXTA-like proteins identified in liverworts have implicated MIXTA in the early evolution of the cuticle formation and therefore the colonization of land by plants (Xu et al., 2021). Because cutin is an important structural component of the trichome, it is possible that CsMIXTA may be coordinating the biosynthesis of this compound in the trichome.

A previous study demonstrated that expression of cannabinoid biosynthetic genes peaked in weeks 4 or 5 (Apicella et al., 2021); CsMIXTA expression showed a similar pattern. It has been shown that trichomes produce most cannabinoids during the latter capitate-stalked glandular phase. Therefore, it is reasonable to propose that the development of the stalk cells also occurs around week 4 of floral development, in correlation with the expression of CsMIXTA.

There is a strong positive correlation between CsMIXTA expression and the expression of both GPPS and OAC, enzymes which synthesize the necessary precursors for both cannabinoids and monoterpenes, GPP and olivetolic acid respectively (Apicella et al., 2021). Sessile (non-stalked) glandular trichomes produce minimal monoterpenes or cannabinoids before maturation, possessing a sesquiterpene-dominant chemotype. However, after the sessile trichomes develop into stalked glandular trichomes (CSG's), cannabinoid and monoterpene biosynthesis takes place. Previous studies have shown that GPPS was more highly expressed in stalked trichomes, but OAC expression was similar among different glandular trichome types (Livingston et al., 2020).

The ectopic overexpression of CsMIXTA in tobacco has shown a significant impact on trichome development with increased density, enlarged size and more branching (FIG. 4). The overexpression of CsMIXTA in tobacco showed distinct trichome phenotypes than that of AmMIXTA overexpression (Glover et al., n.d.; Payne et al., 1999). The overexpression of known MIXTA or MIXTA-like genes did not show a similar glandular trichome phenotype caused by overexpression of CsMIXTA, indicating that CsMIXTA could have peculiar functions in glandular trichome morphogenesis in cannabis. Genetic engineering of CsMIXTA has the potential to promote cannabinoid production by increasing glandular trichome formation.

CONCLUSIONS

CsMIXTA is strongly expressed in inflorescence tissue and has an expression pattern which coordinates with cannabinoid biosynthesis genes. Through analyzing gene expression data, established a clear association between CsMIXTA expression and trichome development/cannabinoid biosynthesis was established. CsMIXTA is also expressed in the isolated trichome, but not as strongly as it is in the whole flower tissue. CsMIXTA expression has a significantly positive correlation with the expression of GPPS and OAC, two important enzymes in the cannabinoid biosynthesis pathway. These data suggest that CsMIXTA is not only involved in glandular trichome initiation and morphogenesis in cannabis, but also cannabinoid biosynthesis, and given MIXTA's function in other species, the biosynthesis of cutin in the trichome. The overexpression of CsMIXTA in tobacco resulted in an increase in trichome density, size and branching on the leaf; this demonstrates that CsMIXTA is a transcription factor which is causal to trichome initiation and morphogenesis. Together, these data provide strong evidence that CsMIXTA is a transcription factor which is causal to the initiation and morphogenesis of CSG's in cannabis female flowers, and instrumental to cannabinoid biosynthesis.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

REFERENCES

Apicella, P. V., Sands, L. B., Ma, Y., Berkowitz, G. A., 2021. Delineating the genetic regulation of cannabinoid biosynthesis during female flower development in Cannabis sativa (preprint). Plant Biology. doi.org/10.1101/2021.11.05.464876

Glover, B. J., Perez-Rodriguez, M., Martin, C., n.d. Development of several epidermal cell types can be specified by the same MYB-related plant transcription factor 12.

Guo, R., Guo, H., Zhang, Q., Guo, M., Xu, Y., Zeng, M., Lv, P., Chen, X., Yang, M., 2018. Evaluation of reference genes for RT-qPCR analysis in wild and cultivated Cannabis. Biosci. Biotechnol. Biochem. 82, 1902-1910. doi.org/10.1080/09168451.2018.1506253

Lashbrooke, J. G., Adato, A., Lotan, O., Alkan, N., Tsimbalist, T., Rechav, K., Fernandez Moreno, J.-P., Widemann, E., Grausem, B., Pinot, F., Granell, A., Costa, F., Aharoni, A., 2015. The Tomato MIXTA-like Transcription Factor Coordinates Fruit Epidermis Conical Cell Development and Cuticular Lipid Biosynthesis and Assembly. Plant Physiol. pp. 01145.2015. doi.org/10.1104/pp. 15.01145

Livingston, S. J., Quilichini, T. D., Booth, J. K., Wong, D. C. J., Rensing, K. H., Laflamme-Yonkman, J., Castellarin, S. D., Bohlmann, J., Page, J. E., Samuels, A. L., 2020. Cannabis glandular trichomes alter morphology and metabolite content during flower maturation. Plant J. 101, 37-56. doi.org/10.1111/tpj.14516

Oshima, Y., Shikata, M., Koyama, T., Ohtsubo, N., Mitsuda, N., Ohme-Takagi, M., 2013. MIXTA-Like Transcription Factors and WAX INDUCER1/SHINE1 Coordinately Regulate Cuticle Development in Arabidopsis and Torenia foumieri. Plant Cell 25, 1609-1624. doi.org/10.1105/tpc.113.110783

Payne, T., Clement, J., Arnold, D., Lloyd, A., 1999. Heterologous myb genes distinct from GL1 enhance trichome production when overexpressed in Nicotiana tabacum. Development 126, 671-682. doi.org/10.1242/dev.126.4.671

Shi, P., Fu, X., Shen, Q., Liu, M., Pan, Q., Tang, Y., Jiang, W., Lv, Z., Yan, T., Ma, Y., Chen, M., Hao, X., Liu, P., Li, L., Sun, X., Tang, K., 2018. The roles of AaMIXTA] in regulating the initiation of glandular trichomes and cuticle biosynthesis in Artemisia annua. New Phytol. 217, 261-276. https://doi.org/10.1111/nph.14789

Uzelac, B., Stojibie, D., Budimir, S., 2021. Glandular Trichomes on the Leaves of Nicotiana tabacum: Morphology, Developmental Ultrastructure, and Secondary Metabolites, in: Ramawat, K. G., Ekiert, H. M., Goyal, S. (Eds.), Plant Cell and Tissue Differentiation and Secondary Metabolites, Reference Series in Phytochemistry. Springer International Publishing, Cham, pp. 25-61. doi.org/10.1007/978-3-030-30185-9_1

Voinnet, O., Rivas, S., Mestre, P., Baulcombe, D., 2003. Retracted: An enhanced transient expression system in plants based on suppression of gene silencing by the p19 protein of tomato bushy stunt virus: An enhanced transient expression system in N. benthamiana. Plant J. 33, 949956. doi.org/10.1046/j.1365-313X.2003.01676.x Xu, B., Taylor, L., Pucker, B., Feng, T., Glover, B. J., Brockington, S. F., 2021. The land plant-specific MIXTA-MYB lineage is implicated in the early evolution of the plant cuticle and the colonization of land. New Phytol. 229, 2324-2338. doi.org/10.1111/nph.16997

Yan, T., Li, L., Xie, L., Chen, M., Shen, Q., Pan, Q., Fu, X., Shi, P., Tang, Y., Huang, H., Huang, Yiwen, Huang, Youran, Tang, K., 2018. A novel HD-ZIP IV/MIXTA complex promotes glandular trichome initiation and cuticle development in *Artemisia annua*. New Phytol. 218, 567-578. doi.org/10.1111/nph.15005

What is claimed is:

1. A recombinant nucleic acid molecule comprising:
   (a) a nucleotide sequence encoding a R2R3-MYB transcription factor from *Cannabis sativa* having the nucleic acid sequence of SEQ ID NO:1; and
   (b) a nucleotide sequence encoding a heterologous promoter, wherein the nucleotide sequence encoding the R2R3-MYB transcription factor is operably linked to the nucleotide sequence encoding the heterologous promoter.

2. The recombinant DNA molecule of claim 1, wherein the promoter is a ubiquitin promoter or a trichome specific promoter.

3. An expression vector comprising the recombinant nucleic acid molecule of claim 1.

4. A genetically engineered host cell comprising the expression vector of claim 3.

5. The genetically engineered host cell of claim 4, wherein the cell is a *Cannabis sativa* cell or a *Nicotiana tabacum* cell.

6. A genetically engineered plant or plant cell comprising a chimeric gene integrated into its genome, the chimeric gene comprising a nucleotide sequence encoding a R2R3-MYB transcription factor and having the nucleic acid sequence of SEQ ID NO: 1 operably linked to homologous or heterologous promoter.

7. The genetically engineered plant or plant cell of claim 6, wherein the promoter is a ubiquitin promoter or a trichome specific promoter.

8. The genetically engineered plant or plant cell of claim 6, wherein the plant or plant cell is *Cannabis sativa*.

9. The genetically engineered plant or plant cell of claim 6, wherein the genetically engineered *Cannabis sativa* produces increased Δ9 tetrahydrocannabinol (THC), cannabichromene (CBC), cannabidiol (CBD), or any combination thereof when compared to a wildtype or control *Cannabis sativa* plant.

10. The genetically engineered plant or plant cell of claim 6, comprising a part of the genetically engineered plant.

11. A method of increasing or upregulating trichome formation in a plant or plant cell, the method comprising the steps of:
    (a) transforming a plant or plant cell with a nucleotide sequence that encodes a R2R3-MYB transcription factor and has the nucleic acid sequence of SEQ ID NO:1; and
    (b) growing the plant or plant cell under conditions which allow for expression of SEQ ID NO: 1, wherein expression of the R2R3-MYB transcription factor in the plant increases or upregulates trichome formation in the plant when compared to a wildtype or control plant.

12. The method of claim 11, wherein
    the plant or plant cell is transformed with an expression vector comprising:
    the nucleotide sequence encoding a R2R3-MYB transcription factor having the nucleic acid sequence of SEQ ID NO: 1; and
    a nucleotide sequence encoding a heterologous promoter, wherein the nucleotide sequence encoding the R2R3-MYB transcription factor is operably linked to the nucleotide sequence encoding a heterologous promoter.

13. The method of claim 12, wherein the promoter is a ubiquitin promoter or a trichome specific promoter.

14. The method of claim 11, wherein the plant or plant cell is *Cannabis sativa* or a *Nicotiana tabacum*.

15. The method of claim 11, wherein the plant or plant cell is transformed using *Agrobacterium* Ti-plasmid mediated transformation.

16. A genetically engineered plant or plant part produced by the method of claim 11.

17. The genetically engineered plant or plant part of claim 16, wherein the plant or plant part is *Cannabis sativa* or a *Nicotiana tabacum*.

18. The genetically engineered plant or plant part of claim 17, wherein the genetically engineered plant or plant part is *Cannabis sativa*, and further wherein said genetically engineered plant or plant part contains increased Δ9 tetrahydrocannabinol (THC), cannabichromene (CBC), cannabidiol (CBD), or any combination thereof when compared to a wildtype or control *Cannabis sativa* plant.

19. A method of increasing cannabinoid formation in a plant or plant cell, the method comprising the steps of:
    (a) transforming a cannabinoid producing plant or plant cell with a nucleotide sequence that encodes a R2R3-MYB transcription factor and has the nucleic acid sequence of SEQ ID NO: 1; and
    (b) growing the plant or plant cell under conditions which allow for expression of the R2R3-MYB transcription factor wherein, expression of the R2R3-MYB transcription factor in the plant: (i) increases or upregulates trichome formation in the plant or plant cell; and (ii) increases or upregulates the formation of a cannabinoid in the plant or plant cell.

20. The method of claim 19, wherein
    the plant or plant cell is transformed with an expression vector comprising:
    the nucleotide sequence encoding a R2R3-MYB transcription factor and having the nucleic acid sequence of SEQ ID NO: 1; and
    a nucleotide sequence encoding a heterologous promoter, wherein the nucleotide sequence encoding the R2R3-MYB transcription factor is operably linked to the nucleotide sequence encoding a heterologous promoter.

21. The method of claim 20, wherein the promoter is a ubiquitin promoter or a trichome specific promoter.

22. The method of claim 19, wherein the plant or plant cell is *Cannabis sativa*.

23. The method of claim 19, wherein the cannabinoid is Δ9 tetrahydrocannabinol (THC), cannabichromene (CBC), cannabidiol (CBD), cannabigerol (CBG), cannabinol (CBN), or any combination thereof.

24. The method of claim 19, wherein the plant or plant cell is transformed using *Agrobacterium* Ti-plasmid mediated transformation.

25. A genetically engineered plant or plant part produced by the method of claim 19.

26. The genetically engineered plant or plant part of claim 25, wherein the plant or plant part is *Cannabis sativa*.

27. The genetically engineered plant or plant part of claim 26, wherein the genetically engineered plant or plant part is *Cannabis sativa*, and further wherein said genetically engineered plant or plant part contains increased Δ9 tetrahydrocannabinol (THC), cannabichromene (CBC), cannabidiol (CBD), or any combination thereof when compared to a wildtype or control *Cannabis sativa* plant.

\* \* \* \* \*